US011406711B2

(12) United States Patent
Creighton

(10) Patent No.: US 11,406,711 B2
(45) Date of Patent: Aug. 9, 2022

(54) SYSTEM AND METHOD FOR CONVEYANCE OF THERAPEUTIC AGENTS USING A CONFIGURABLE MAGNETIC FIELD

(71) Applicant: UNandUP, LLC., Saint Louis, MO (US)

(72) Inventor: Francis M. Creighton, St. Louis, MO (US)

(73) Assignee: UNANDUP, LLC., Saint Louis, MO (US)

( * ) Notice: Subject to any disclaimer, the term of this patent is extended or adjusted under 35 U.S.C. 154(b) by 356 days.

(21) Appl. No.: 16/389,476

(22) Filed: Apr. 19, 2019

(65) Prior Publication Data

US 2019/0321472 A1    Oct. 24, 2019

Related U.S. Application Data

(60) Provisional application No. 62/660,614, filed on Apr. 20, 2018.

(51) Int. Cl.
*A61K 41/00* (2020.01)
*A61N 2/06* (2006.01)

(52) U.S. Cl.
CPC ............. *A61K 41/00* (2013.01); *A61N 2/06* (2013.01)

(58) Field of Classification Search
CPC ........ A61K 41/00; A61K 9/0009; A61N 2/06; A61M 2207/00; A61M 2205/3317; A61M 2205/0272; A61M 37/00
USPC ................................. 128/897–899; 600/9–15
See application file for complete search history.

(56) References Cited

U.S. PATENT DOCUMENTS

| | | | |
|---|---|---|---|
| 8,308,628 B2 | 5/2012 | Creighton |
| 8,313,422 B2 | 11/2012 | Creighton |
| 8,529,428 B2 | 9/2013 | Creighton |
| 8,715,150 B2 | 5/2014 | Creighton |
| 8,926,491 B2 | 1/2015 | Creighton |
| 9,345,498 B2 | 5/2016 | Creighton |
| 9,883,878 B2 | 2/2018 | Creighton |
| 10,029,008 B2 | 7/2018 | Creighton |
| 10,149,734 B2 | 12/2018 | Creighton |

(Continued)

*Primary Examiner* — Sunita Reddy
(74) *Attorney, Agent, or Firm* — Blynn L. Shideler; Krisanne Shideler; BLK Law Group

(57) ABSTRACT

A system and method for therapeutic agent conveyance using configurable magnetic field includes a field generating workstation. The workstation includes at least one, generally a pair of, magnet subassemblies. Each subassembly is rotationally mounted on a rotation axis to orientate the subassembly poles. A rotatable yoke supports each subassembly and the yoke axis is offset from each subassembly rotation axis. Yoke rotation configures a collective system magnetic field. The method aligns the yoke axis with a user selected region within a subject, introduces a plurality of magnetic materials and associated therapeutic agents into the subject; orientates each magnet subassembly at a specific angular location and configures the workstations magnetic field whereby the plurality of magnetic materials and associated therapeutic agents are influenced by the magnetic field to either be simultaneously conveyed towards the user-selected region from multiple directions or simultaneously conveyed away from a user-selected region in multiple directions.

17 Claims, 12 Drawing Sheets

(56) References Cited

U.S. PATENT DOCUMENTS

| | | | |
|---|---|---|---|
| 2004/0112468 A1* | 6/2004 | Petzold | H01F 1/15333 |
| | | | 148/121 |
| 2006/0142748 A1* | 6/2006 | Foreman | A61N 2/02 |
| | | | 606/27 |
| 2007/0258907 A1* | 11/2007 | Davis | B82Y 5/00 |
| | | | 424/9.322 |
| 2011/0015464 A1* | 1/2011 | Riehl | A61N 2/006 |
| | | | 600/9 |
| 2011/0112427 A1* | 5/2011 | Phillips | A61N 2/008 |
| | | | 600/544 |
| 2015/0230810 A1* | 8/2015 | Creighton | A61K 41/0028 |
| | | | 604/518 |

* cited by examiner

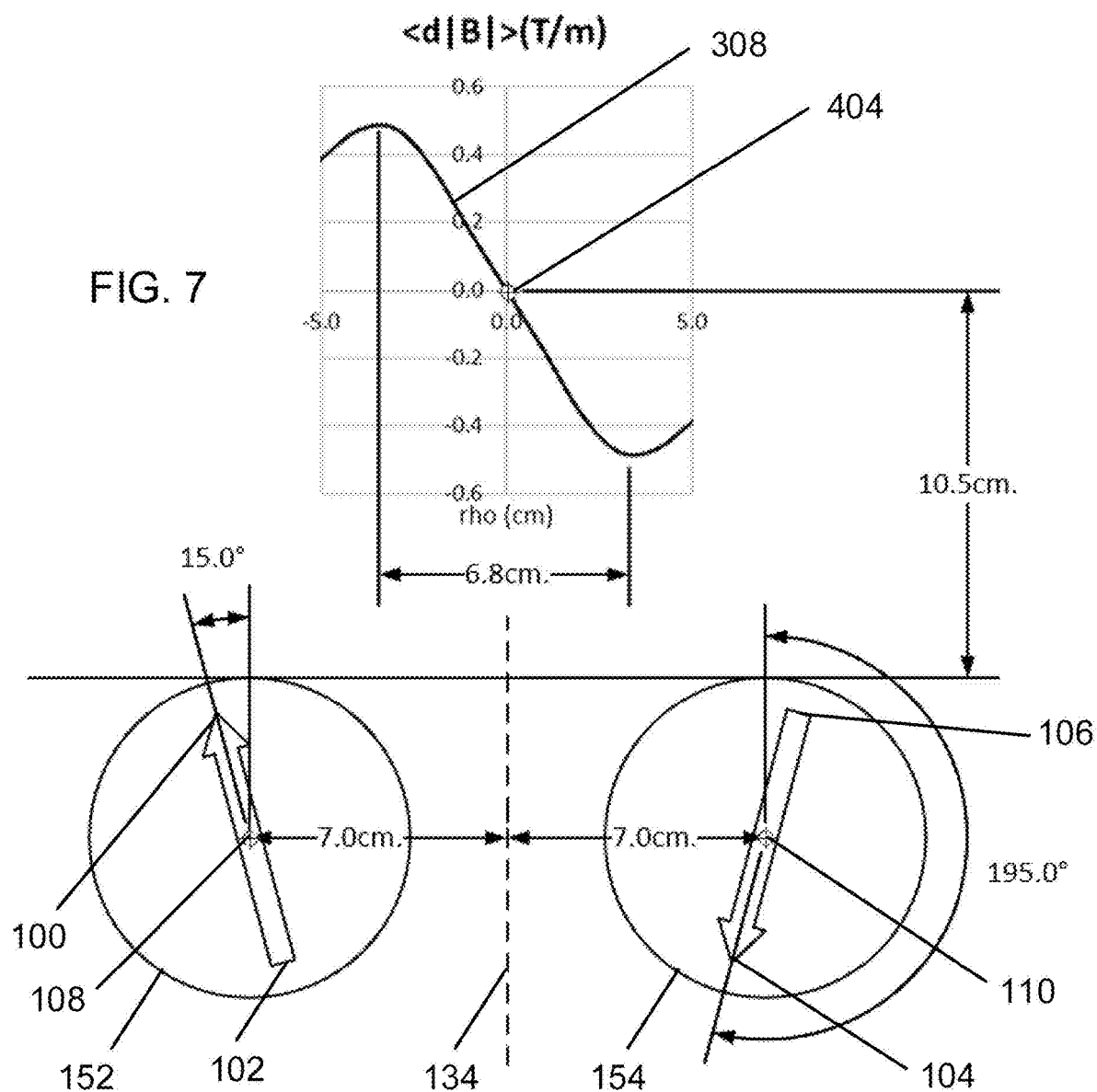

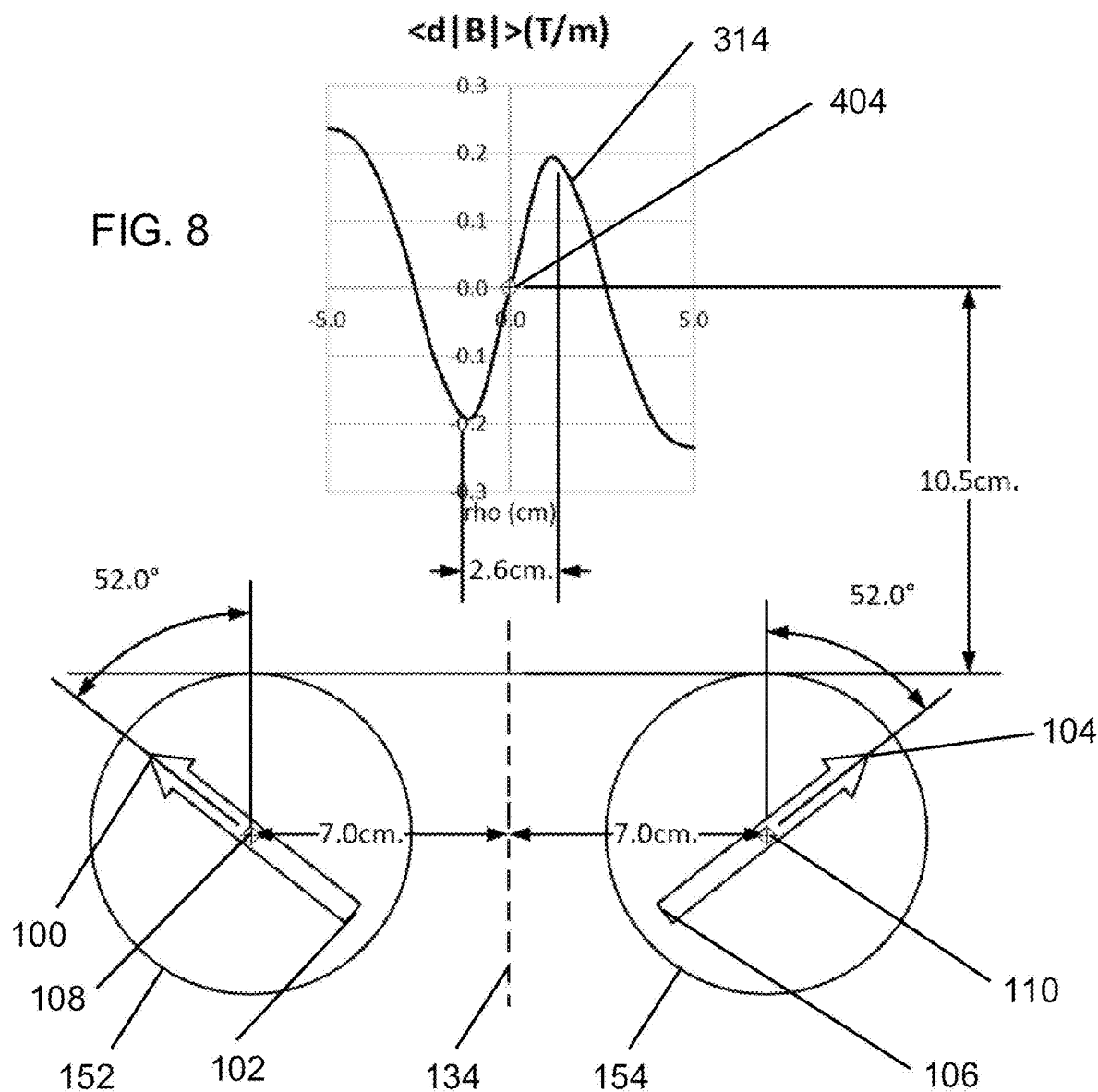

SYSTEM AND METHOD FOR CONVEYANCE OF THERAPEUTIC AGENTS USING A CONFIGURABLE MAGNETIC FIELD

RELATED APPLICATIONS

This application claims priority to U.S. Patent Application Ser. No. 62/660,614, filed Apr. 20, 2018 entitled "Conveyance of Magnetic Materials for Therapeutic Delivery using Optimal Magnet States" which is incorporated herein by reference.

BACKGROUND INFORMATION

1. Field of the Invention

The present invention relates to conveyance of therapeutic and related materials within the body through magnetic fields.

2. Background Information

The use of magnetic fields in medicine is not new. In 1873, Dr. Julius Hirschberg is often credited with being the first to use an electromagnet to remove iron filings from the eye. From that time onward, magnetism in medicine quickly expanded, including uses of iron compounds to deliver hyperthermia for tumors in 1957, thrombosis inducement within aneurysm sacks in 1965, embolization of tumors in 1973, and to enhanced imaging for MR procedures in 1982, to name a few milestones. Excitement was driven by the long safety history of carbonyl iron and other iron oxides, including magnetite, with regard to cytotoxicity, irritation, skin sensitization, acute systemic toxicity, pyrogenicity, genotoxicity, carcinogenicity, reproductive/developmental toxicity, and interactions with blood. Iron-containing particles are primarily sequestered by the liver and spleen. After sequestration, iron is regulated by the body's clearance mechanisms which rely on transferrin and ferritin to shuttle and store the resulting iron ions, where iron biodegradation follows the same mechanisms involved in intracellular degradation of ferritin.

For magnetic navigation, the complexities associated with scaling magnetic systems were a barrier to most commercial efforts attempting magnetically-directed iron particle therapy due to an overreliance on magnetic force to pull iron particles, which falls off to the $4^{th}$ power of distance for magnetically saturated materials, and the $7^{th}$ power for magnetically unsaturated materials. For example, while pulling iron particles works well when the magnet's center is less than 1 cm away from the target, increasing the distance to 5 cm results in a 600-fold increase in the magnet strength needed to generate the same pulling force. For this reason, many commercial efforts have failed given the high cost, increased complexity, and large footprint of the external magnetic field-generating device.

Pulse Therapeutics, Inc. of St. Louis, Mo. developed technology designed to deliver magnetic nanoparticle agglomerates to a clot. The technology essentially consists of a single magnet which is positioned and articulated so that nanoparticle agglomerates are formed, which are delivered to the desired location in an end-over-end motion. This technology is collectively set forth in U.S. Pat. No. 10,149,734 titled "Magnetic Particle Control and Visualization", U.S. Pat. No. 10,029,008 titled Therapeutic Magnetic Control Systems and Contrast Agents", U.S. Pat. No. 9,883,878 titled "Magnetic-based systems and methods for manipulation of magnetic particles", U.S. Pat. No. 9,345,498 titled "Methods of controlling magnetic nanoparticles to improve vascular flow", U.S. Pat. No. 8,926,491 titled "Controlling magnetic nanoparticles to increase vascular flow", U.S. Pat. No. 8,715,150 titled "Devices for controlling magnetic nanoparticles to treat fluid obstructions", U.S. Pat. No. 8,529,428 titled "Methods of controlling magnetic nanoparticles to improve vascular flow", U.S. Pat. No. 8,313,422 titled "Magnetic-based methods for treating vessel obstructions", and U.S. Pat. No. 8,308,628 titled "Magnetic-based systems for treating occluded vessels" which are incorporated herein by reference. The Pulse Therapeutics patents are incorporated herein by reference and this technology represents great potential and substantial improvements over earlier technologies. However there remain a number of serious drawbacks represented in this Pulse Therapeutics technology as disclosed.

The most significant limitation of the Pulse Therapeutics technology is that the direction of nanoparticle conveyance must be specified in advance, a single magnet must be used, and nanoparticle conveyance occurs only in one direction along a "directed gradient". Thus, this technology is unable to simultaneously convey magnetic materials in multiple directions or from multiple directions. Further, the Pulse Therapeutics technology is primarily directed toward the use of "nanoparticles" and can be limiting in the size of therapeutic materials conveyed. The Pulse Therapeutics technology is generally directed to the creation and movement of agglomerates of magnetic materials, which can be unduly restrictive in particle motion.

There remains a need in the art for greater control of therapeutic agent movement with magnetic fields.

SUMMARY OF THE INVENTION

One aspect of this invention is directed to a system for conveyance of therapeutic agents using a configurable magnetic field including at least one magnet subassembly, and preferably pairs of magnet subassemblies, each magnet subassembly with a north magnetic pole and south magnetic pole, wherein each magnet subassembly is mounted for rotation about a magnet subassembly rotation axis that varies the orientation of the north magnetic pole and south magnetic pole of the magnet subassembly; a yoke supporting each magnet subassembly and mounted for rotation about a yoke axis that is offset from each magnet subassembly rotation axis, wherein rotation of the yoke configures a collective magnetic field of the system; and a plurality of magnetic materials associated with therapeutic agents to be conveyed by the system.

One aspect of the present invention is directed to a method for conveyance of therapeutic agents using a configurable magnetic field including providing a magnetic field generating workstation comprising at least one magnet subassembly, each magnet subassembly with a north magnetic pole and south magnetic pole, wherein each magnet subassembly is mounted for rotation about a magnet subassembly rotation axis that varies the orientation of the north magnetic pole and south magnetic pole of the magnet subassembly, and a yoke supporting each magnet subassembly and mounted for rotation about a yoke axis that is offset from each magnet subassembly rotation axis, wherein rotation of the yoke configures a collective magnetic field of the system; aligning the yoke with a user selected region within a subject; introducing a plurality of magnetic materials and associated therapeutic agents to be conveyed by the system into the subject; orientating each magnet subassembly by rotation about a magnet subassembly rotation axis to a specific angular location and configuring the magnetic field of the magnetic field generating workstation by rotation of the yoke about the yoke axis whereby the plurality of magnetic materials and associated therapeutic agents to be conveyed by the system are influenced by the magnetic field to either be simultaneously conveyed towards the user-selected region from multiple directions or simultaneously conveyed away from a user-selected region in multiple directions.

The features that characterize the present invention are pointed out with particularity in the claims which are part of this disclosure. These and other features of the invention, its operating advantages and the specific objectives obtained by its use will be more fully understood from the following detailed description in connection with the attached figures.

BRIEF DESCRIPTION OF THE FIGURES

FIG. 7 is a schematic representation of one example of permanent magnet angulations of the magnets of the system of 1A-B which achieve a time-averaged gradient that collects magnetic materials to a desired point in space for a magnetic material collection conveyance method in accordance with one aspect of the present invention; and FIG. 8 is a schematic representation of one example of permanent magnet angulations of the magnets of the system of 1A-B which achieve a time-averaged gradient that disperses magnetic materials to a desired point in space for a magnetic material dispersal conveyance method in accordance with one aspect of the present.

DETAILED DESCRIPTION OF THE PREFERRED EMBODIMENTS

Figure 1A:
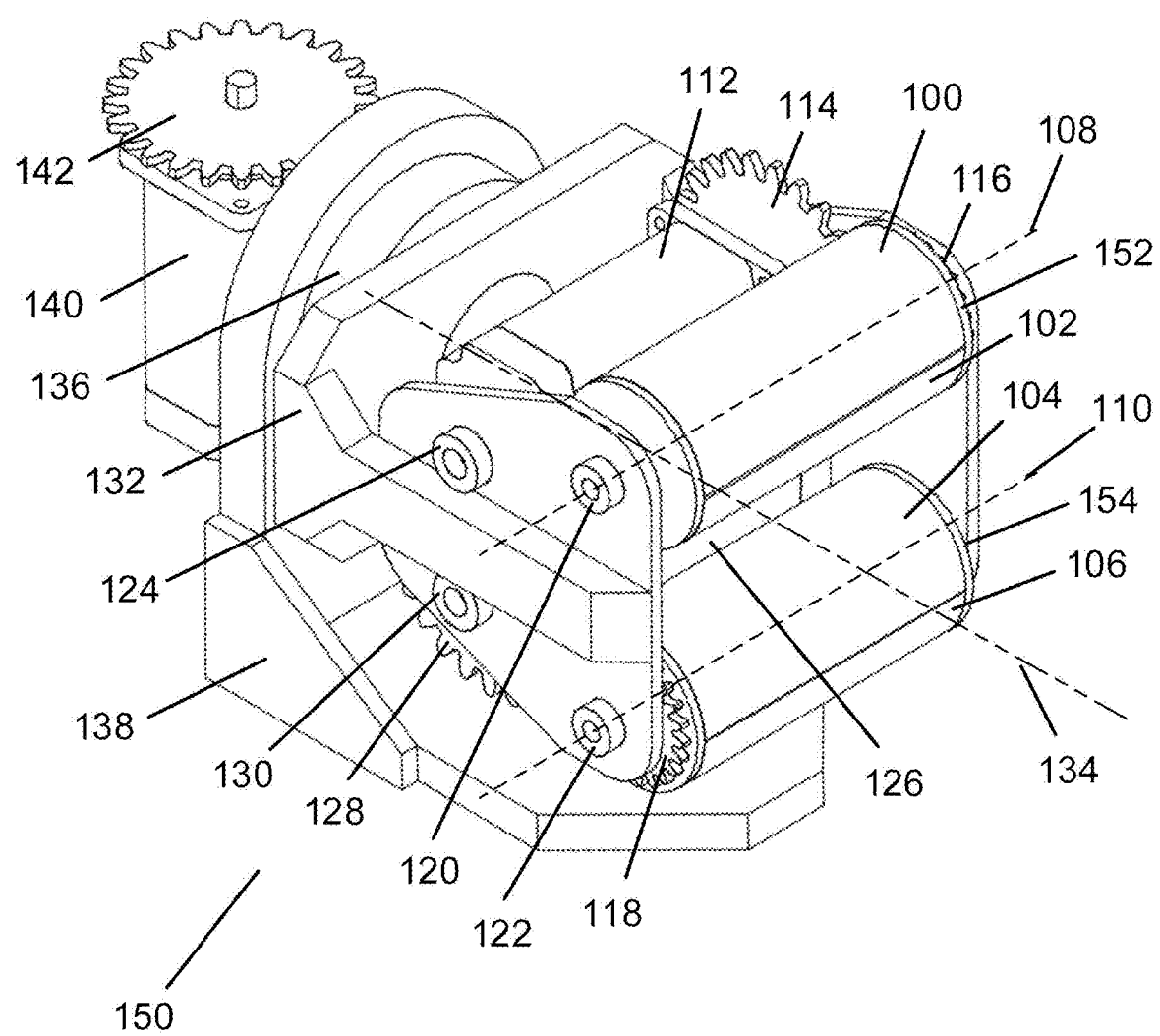
FIG. 1A is a perspective front view of a system for generating user configurable magnetic fields for conveyance of therapeutic and related agents in accordance with one embodiment of the present invention.

The present invention relates to a system and method for conveyance of therapeutic and related agents using configurable magnetic fields. FIG. 1A is a perspective front view of a system or workstation 150 for generating user configurable magnetic fields for conveyance of therapeutic agents in accordance with one embodiment of the present invention The system or workstation 150 is composed of a two-permanent magnet assembly. The first permanent magnet subassembly 152 is composed of permanent magnetic material oriented with a common or aligned north magnetic pole 100 and south magnetic pole 102. In this embodiment, the first permanent magnet subassembly 152 is rotated about first permanent magnet subassembly rotation axis 108 that is perpendicular to the axis between the north magnetic pole 100 and south magnetic pole 102. Rotation of the first permanent magnet subassembly 152 is enabled by a first permanent magnet subassembly bearing 120 and an attached gear 116 which are driven by an actuator formed by a first permanent magnet subassembly motor 112 which is attached to a dedicated drive gear 114. The first permanent magnet subassembly's motor 112 is secured to the yoke 132 via an attachment point 124 on the yoke 132.

The second permanent magnet subassembly 154 is composed of permanent magnetic material oriented with a common or aligned north magnetic pole 104 and south magnetic pole 106, and preferably is the same strength as the permanent magnet subassembly 152. In this embodiment, the second permanent magnet subassembly 154 is rotated about second permanent magnet subassembly axis 110 which is spaced from and parallel to the first permanent magnet subassembly rotation axis 108. Rotation of the second permanent magnet subassembly 154 is enabled by an actuator formed by a second permanent magnet subassembly bearing 122 and an attached gear 118 which are driven by the second permanent magnet subassembly motor 126 which is attached to a dedicated drive gear 128. The second permanent magnet subassembly motor 126 is secured to the yoke 132 via an attachment point 130 on the yoke 132. The yoke 132 can be rotated about the yoke axis 134, which is enabled by provision of a yoke bearing 136 and driven by an actuator formed by a yoke motor 140 attached to a yoke gear drive 142 meshing with a yoke gear 146 (shown in FIG. 1B). The entire substructure of the system 150 rests upon a base 138.

Figure 1B:
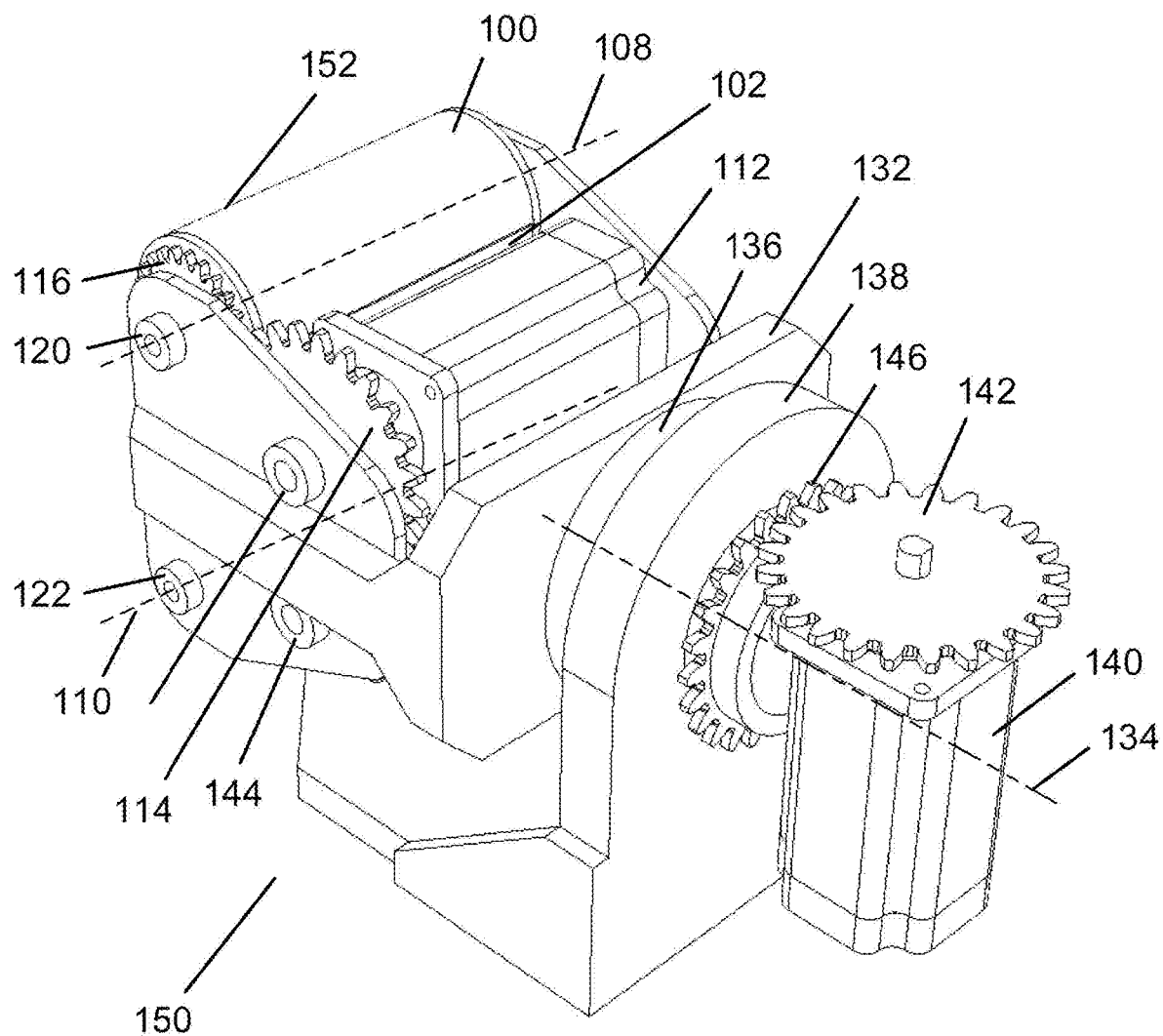
FIG. 1B is a perspective rear view of the system for generating user configurable magnetic fields for conveyance of therapeutic and related agents of FIG. 1A.

FIG. 1B is a perspective rear view of the system 150 for generating user configurable magnetic fields for conveyance of therapeutic agents of FIG. 1A. As seen, the first permanent magnet subassembly 152 is visible, as is the first permanent magnet subassembly north magnetic pole 100. Also seen are the first permanent magnet subassembly rotation axis 108, the second permanent magnet subassembly rotation axis 110, the first permanent magnet subassembly motor 112, the first permanent magnet subassembly motor gear 114, the first permanent magnet subassembly gear 116, the first permanent magnet subassembly bearing 120, the second permanent magnet subassembly bearing 122, the yoke 132, the yoke axis 134, the yoke bearing 136, the base 138, the yoke motor 140, and the yoke motor gear 142. New features visible in FIG. 1B include the second permanent magnet subassembly motor attachment point 144 and the yoke gear 146.

In operation, the desired second spatial derivative of the magnetic field is enabled via angulation of the first permanent magnet subassembly 152 and the second permanent magnet subassembly 154. For the first permanent magnet subassembly 152, the first permanent magnet subassembly motor 112 rotates the first permanent magnet subassembly motor gear 114, which engages the first permanent magnet subassembly gear 116 resulting in a rotation of the first permanent magnet subassembly 152 about the first permanent magnet rotation axis 108. For the second permanent magnet subassembly 154, the second permanent magnet subassembly motor 126 rotates the second permanent magnet subassembly motor gear 128, which engages the second permanent magnet subassembly gear 118 resulting in a rotation of the second permanent magnet subassembly 154 about the second permanent magnet rotation axis 110. The first permanent magnet subassembly 152 and the second permanent magnet subassembly 154 are attached to the yoke 132, which enables rotation of the first and second magnets about the yoke axis 134. The first permanent magnet rotation axis 108 and the second permanent magnet rotation axis 110 are preferably equidistant from the yoke axis 134 and parallel to each other and aligned in a common plane which is perpendicular to the yoke axis 134. For this, the yoke motor 140 rotates the yoke motor gear 142, which engages the yoke gear 146 connected to the yoke 132. This enables rotation control of the yoke 132 about the yoke axis 134 and achieves the desired time-averaged magnetic gradient for magnetic material collection conveyance method 308 or magnetic material dispersal conveyance method 314, as detailed further below.

Figure 2:
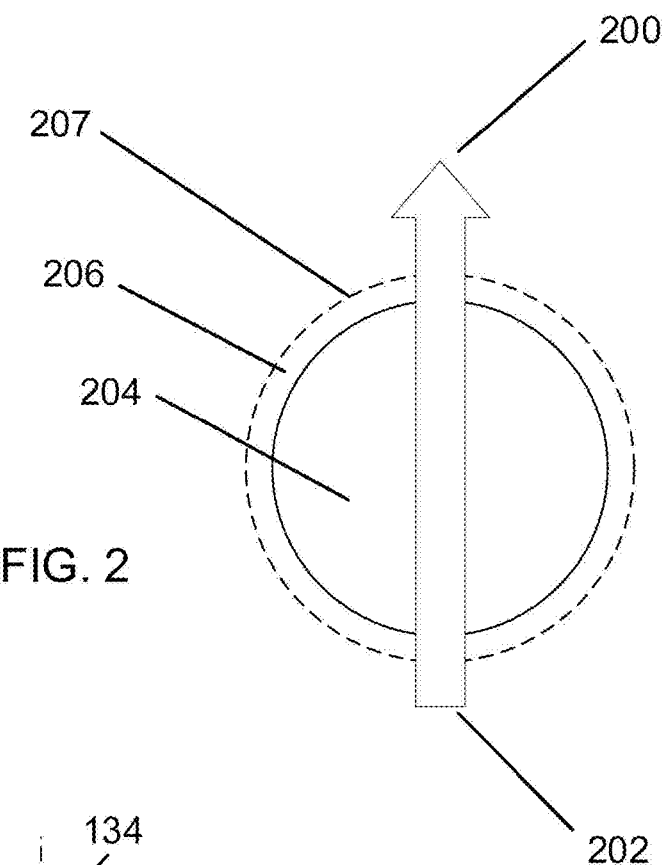
FIG. 2 is a schematic representation of a magnetic material therapeutic agent in accordance with one aspect of the present invention for use with the system of FIGS. 1A-B in which a nonmagnetic coating is applied to a magnetic core that is composed of a single crystalline domain.

FIG. 2 is a schematic representation of a magnetic material therapeutic agent in accordance with one aspect of the present invention for use with the system 150 of FIGS. 1A-B referenced as coated magnetic core 207 in which a nonmagnetic coating 206 is applied to a magnetic core material 204 that is composed of a single crystalline domain. It is noted that the present invention also anticipates a product with multi-domain cores too, such as may be described generally as a plurality of magnetic particles for which the number of magnetic domains is minimal. In this representation, the magnetic core material 204 retains a strong magnetization oriented from the magnetic south pole 202 to the magnetic north pole 200. In one embodiment, the magnetic core material is composed of magnetite iron oxide (chemical form of $Fe_3O_4$) with a single-crystalline phase which is magnetically oriented so as to result in a strong magnetization oriented from the magnetic south pole 202 to the magnetic north pole 200.

In another embodiment, the magnetic core material is composed of magnetite iron oxide (chemical form of $Fe_3O_4$) with multiple crystalline cores which are magnetically oriented so as to result in a strong magnetization oriented from the magnetic south pole 202 to the magnetic north pole 200. For all embodiments, and optional nonmagnetic core coating 206 is used when it is necessary to improve biological compatibility, extend blood plasma half-life, produce favorable magnetic behavior, reduce the potential of agglomerations when not desired, and to serve as a scaffold for attachment of other useful agents. Examples of such useful agents include pharmaceuticals and contrast agents. The collective elements define the coated magnetic core 207.

Figure 3A:
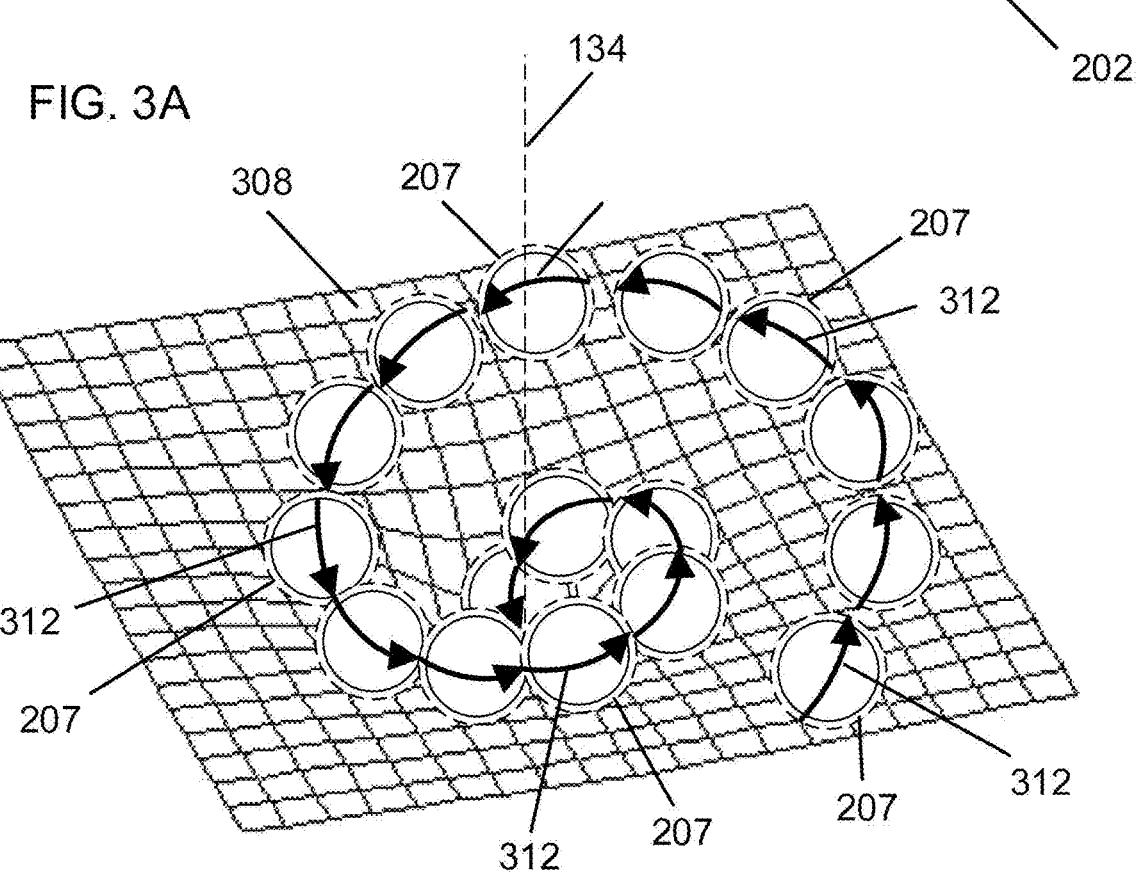
FIG. 3A is a schematic representation of a magnetic material collection conveyance method using a counterclockwise perturbation of the external magnetic field formed by the system of 1A-B in accordance with one aspect of the present invention.

FIG. 3A is a schematic representation of a magnetic material collection conveyance method 308 (also visualized as grid 308) using a counterclockwise perturbation of the external magnetic field formed by the system 150 of 1A-B in accordance with one aspect of the present invention. For this method, the workstation 150 creates the desired time-averaged spatial gradient by minimizing the time-averaged second spatial dimension derivative of the magnetic field (which is also negative in value) using a clockwise rotation of the yoke 132 about the yoke axis 134, which is aligned with the target region. The time-averaged magnetic gradient for collecting coated magnetic materials or cores 207 is visualized as an inwardly curved grid 308. In this example, the clockwise rotation of the yoke 132 about the yoke axis 134 results in the coated magnetic cores 207 rolling or tumbling in a counterclockwise motion 312 towards the target region, which corresponds to the lowest point of the depression.

Figure 3B:
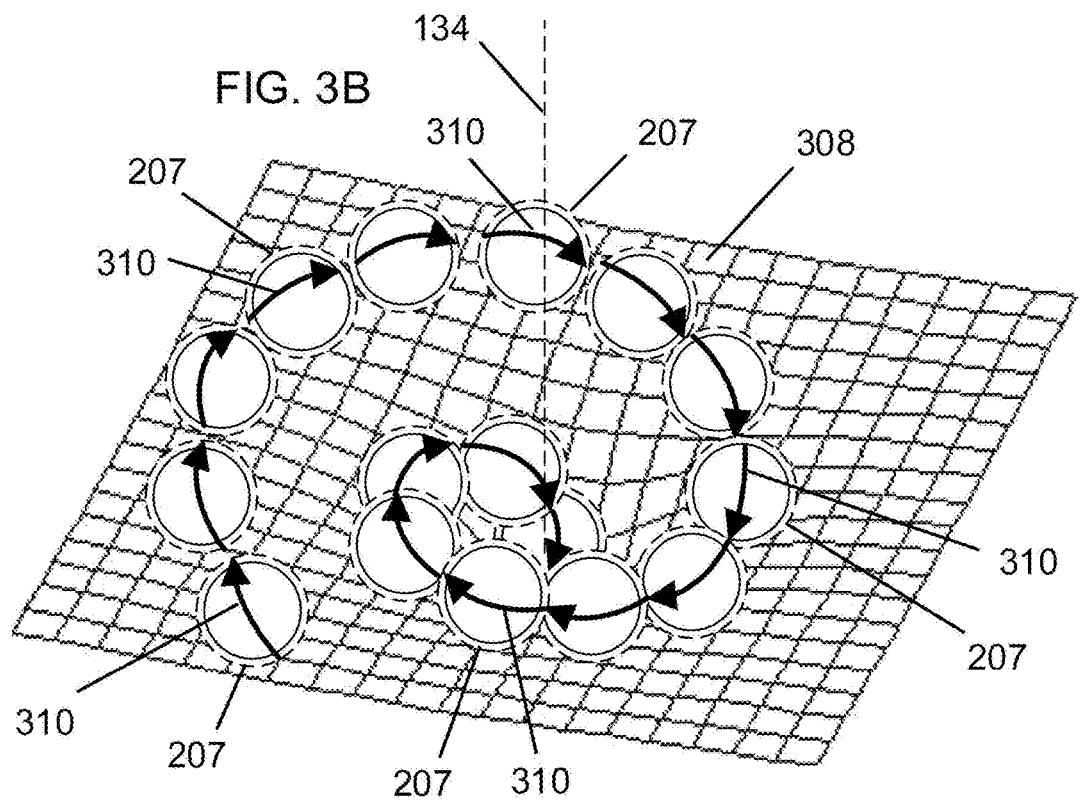
FIG. 3B is a schematic representation of a magnetic material collection conveyance method using a clockwise perturbation of the external magnetic field formed by the system of 1A-B in accordance with one aspect of the present invention.

FIG. 3B is a schematic representation of a magnetic material collection conveyance method 308 (also visualized as grid 308) using a clockwise perturbation of the external magnetic field formed by the system 150 of 1A-B in accordance with one aspect of the present invention. For this method, the workstation 150 creates the desired time-averaged spatial gradient by minimizing the time-averaged second spatial dimension derivative of the magnetic field (which is also negative in value) using a counterclockwise rotation of the yoke 132 about the yoke axis 134, which is aligned with the target region. The time-averaged magnetic gradient for collecting coated magnetic materials or cores 207 is visualized as an inwardly curved grid 308. In this example, the counterclockwise rotation of the yoke 132 about the yoke axis 134 results in the coated magnetic cores 207 rolling or tumbling in a clockwise motion 310 towards the target region, which corresponds to the lowest point of the depression.

Figure 3C:
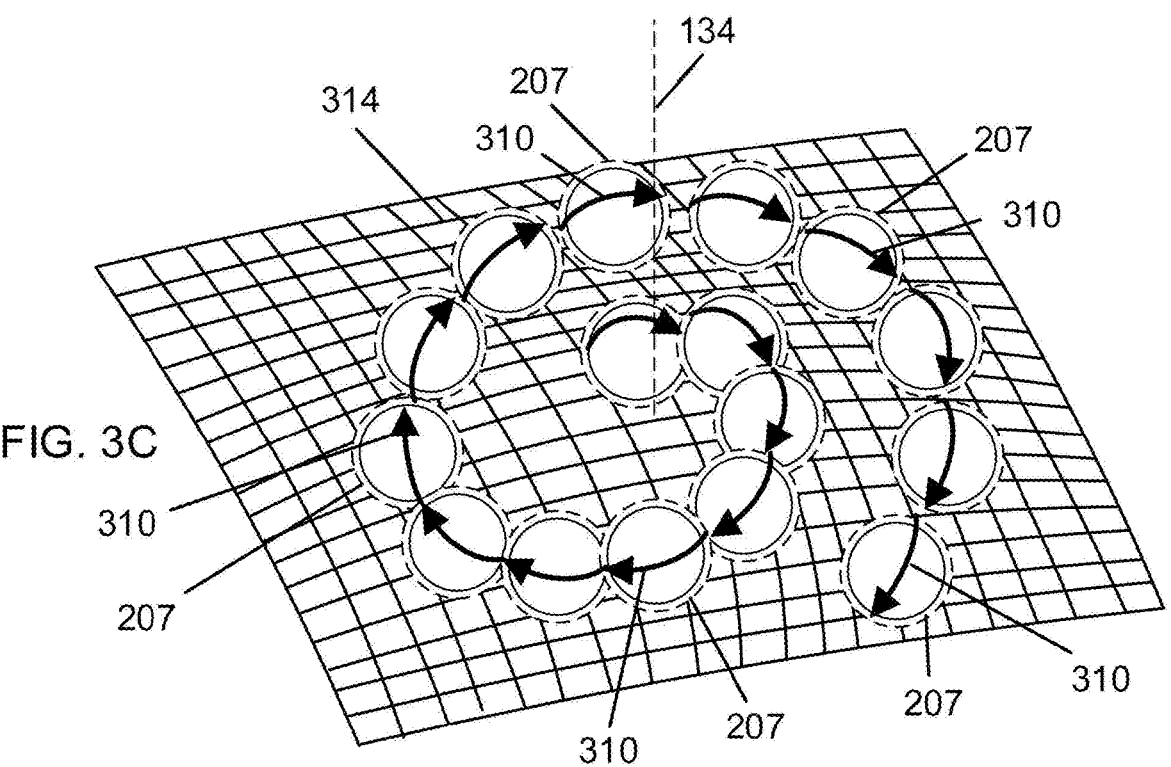
FIG. 3C is a schematic representation of a magnetic material dispersal conveyance method using a clockwise perturbation of the external magnetic field formed by the system of 1A-B in accordance with one aspect of the present invention.

FIG. 3C is a schematic representation of a magnetic material dispersal conveyance method 314 (also visualized as grid 314) using a clockwise perturbation of the external magnetic field formed by the system 150 of 1A-B in accordance with one aspect of the present invention. For this method, the workstation 150 creates the desired time-averaged spatial gradient by maximizing the time-averaged second spatial dimension derivative of the magnetic field (which is also positive in value) using a counterclockwise rotation of the yoke 132 about the yoke axis 134, which is aligned with the target region. The time-averaged magnetic gradient for dispersing coated magnetic materials or cores 207 is visualized as an outwardly curved grid 314. In this example, the counterclockwise rotation of the yoke 132 about the yoke axis 134 results in the coated magnetic cores 207 rolling or tumbling in a clockwise motion 310 away from the target region, which corresponds to the highest point of the raised region.

Figure 3D:
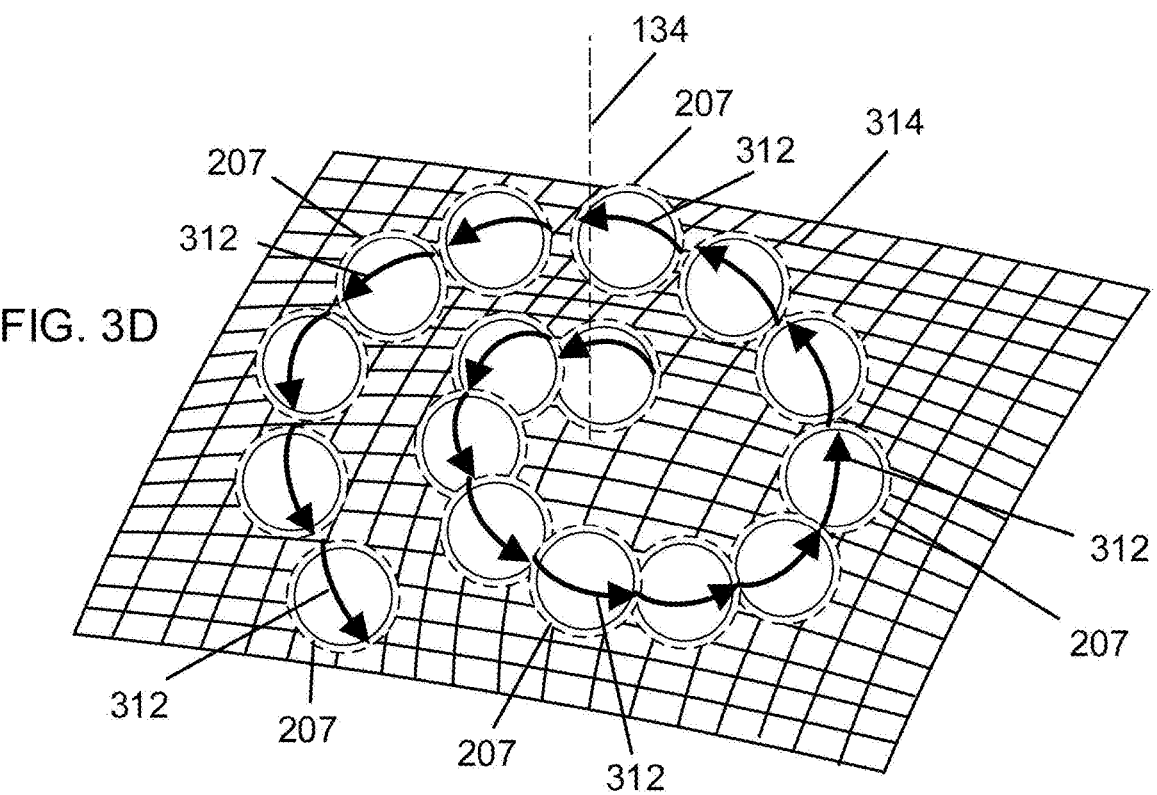
FIG. 3D is a schematic representation of a magnetic material dispersal conveyance method using a counterclockwise perturbation of the external magnetic field formed by the system of 1A-B in accordance with one aspect of the present invention.

FIG. 3D is a schematic representation of a magnetic material dispersal conveyance method 314 (also visualized as grid 314) using a counterclockwise perturbation of the external magnetic field formed by the system 150 of 1A-B in accordance with one aspect of the present invention. For this method, the workstation 150 creates the desired time-averaged spatial gradient by maximizing the time-averaged second spatial dimension derivative of the magnetic field (which is also positive in value) using a clockwise rotation of the yoke 132 about the yoke axis 134, which is aligned with the target region. The time-averaged magnetic gradient for dispersing coated magnetic materials or cores 207 is visualized as an outwardly curved grid 314. In this example, the clockwise rotation of the yoke 132 about the yoke axis 134 results in the coated magnetic cores 207 rolling or tumbling in a counterclockwise motion 312 away from the target region, which corresponds to the highest point of the raised region.

Figure 3E:
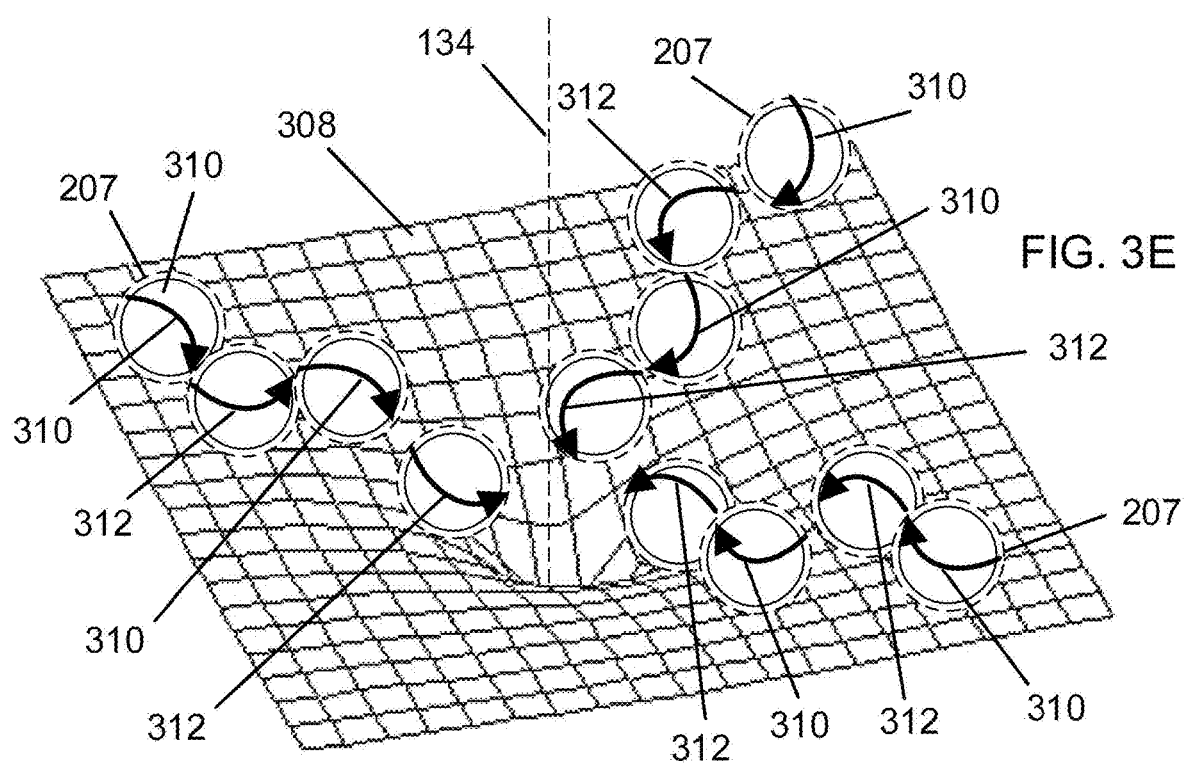
FIG. 3E is a schematic representation of a magnetic material collection conveyance method using both a clockwise and a counterclockwise perturbation of the external magnetic field formed by the system of 1A-B in accordance with one aspect of the present invention.

FIG. 3E is a schematic representation of a magnetic material collection conveyance method 308 (also visualized as grid 308) using both a clockwise and a counterclockwise perturbation of the external magnetic field formed by the system 150 of 1A-B in accordance with one aspect of the present invention. For this method, the workstation 150 creates the desired time-averaged spatial gradient by minimizing the time-averaged second spatial dimension derivative of the magnetic field (which is also negative in value) using both clockwise and counterclockwise rotations of the yoke 132 about the yoke axis 134, which is aligned with the target region. The time-averaged magnetic gradient for collecting coated magnetic materials is visualized as an inwardly curved grid 308. In this example, the clockwise and counterclockwise rotations of the yoke 132 about the yoke axis 134 results in the coated magnetic cores 207 oscillating, rolling, or tumbling in a sequence of clockwise 310 and counterclockwise motions 312 towards the target region, which corresponds to the lowest point of the depression. This method enables magnetic materials or cores 207 to be collected from all radial directions centered on the target region.

Figure 3F:
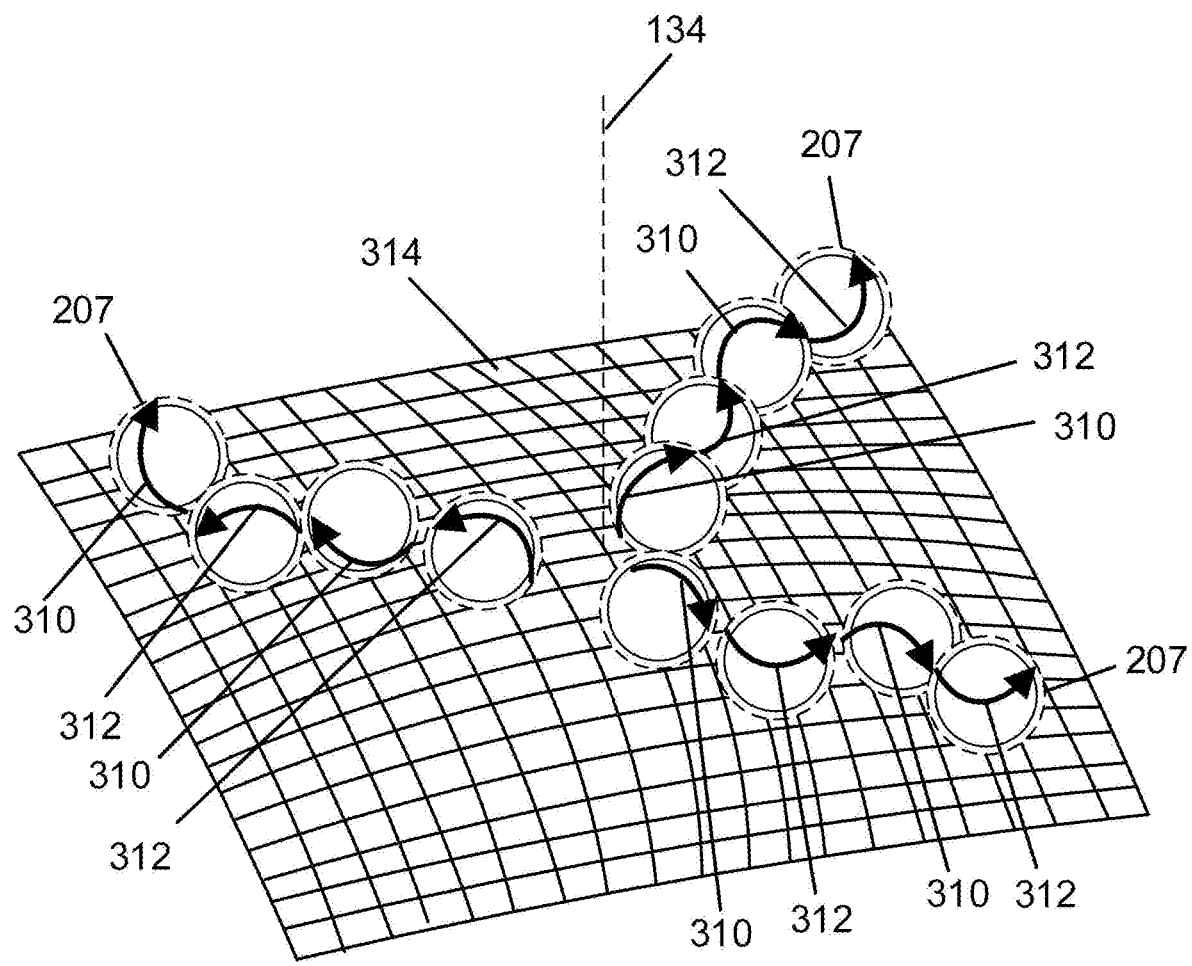
FIG. 3F is a schematic representation of a magnetic material dispersal conveyance method using both a clockwise and a counterclockwise perturbation of the external magnetic field formed by the system of 1A-B in accordance with one aspect of the present invention.

FIG. 3F is a schematic representation of a magnetic material dispersal conveyance method 314 (also visualized as grid 314) using both a clockwise and a counterclockwise perturbation of the external magnetic field formed by the system 150 of 1A-B in accordance with one aspect of the present invention. For this method, the workstation 150 creates the desired time-averaged spatial gradient by maximizing the time-averaged second spatial dimension derivative of the magnetic field (which is also positive in value) using both clockwise and counterclockwise rotations of the yoke 132 about the yoke axis 134, which is aligned with the target region. The time-averaged magnetic gradient for dispersing coated magnetic materials or cores 207 is visualized as an outwardly curved grid 314. In this example, the clockwise and counterclockwise rotations of the yoke 132 about the yoke axis 134 results in the coated magnetic cores 207 oscillating, rolling, or tumbling in a sequence of clockwise 310 and counterclockwise motions 312 away from the target region, which corresponds to the highest point of the raised region. This method enables magnetic materials or cores 207 to be dispersed in all radial directions centered on the target region.

Figure 4A:
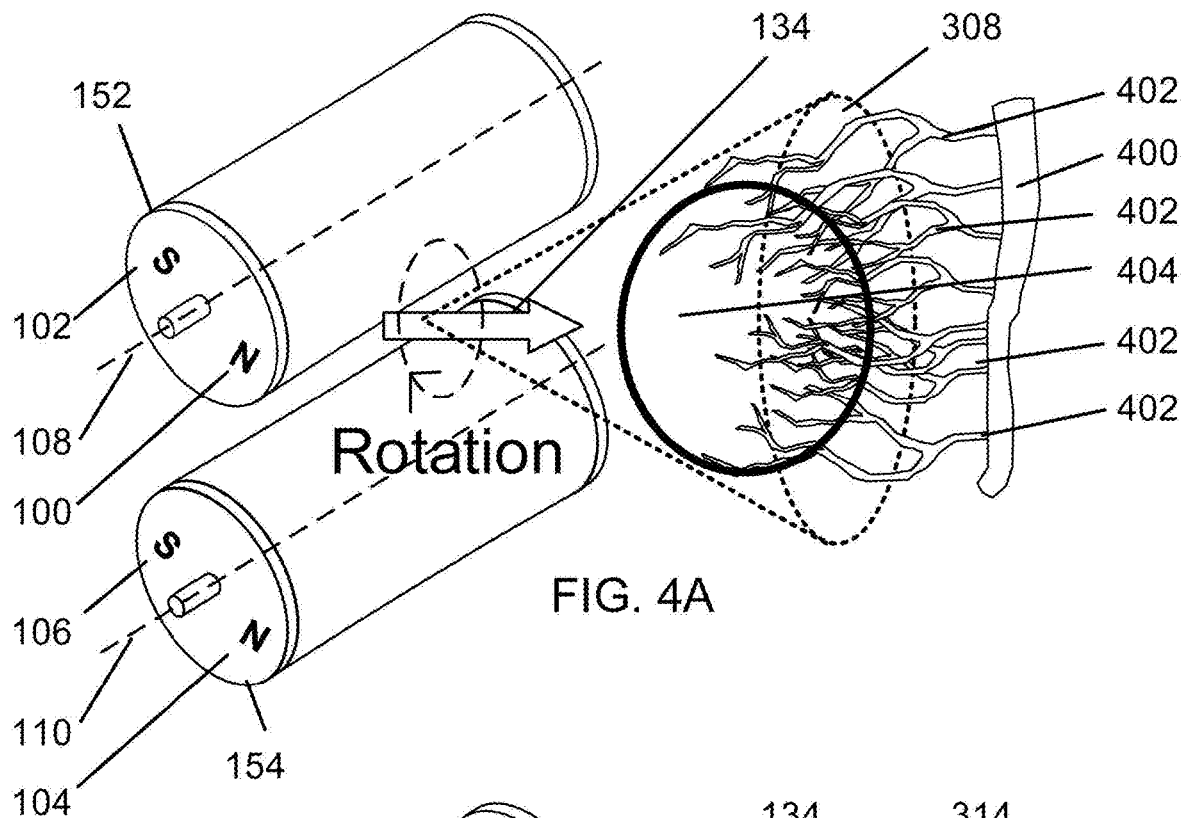
FIG. 4A is a schematic perspective view of a magnetic material collection conveyance method within a desired vascularized region using perturbations of the external magnetic field formed by the system of 1A-B in accordance with one aspect of the present invention.
Figure 4B:
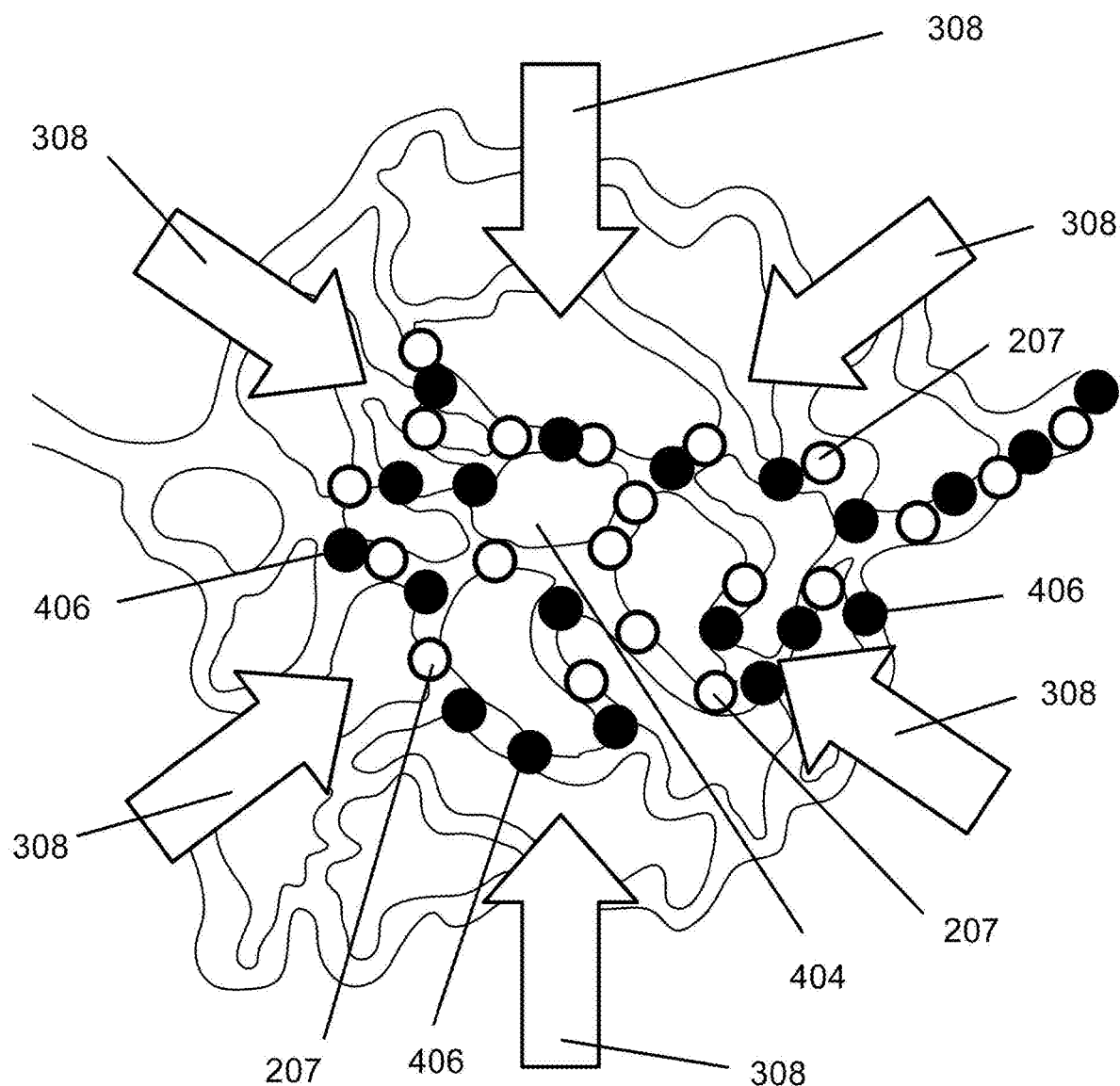
FIG. 4B is a schematic representation of the magnetic material collection conveyance method of FIG. 4A.

FIG. 4A is a schematic perspective view of a magnetic material collection conveyance method 308 within a desired vascularized region using perturbations of the external magnetic field formed by the system 150 of 1A-B in accordance with one aspect of the present invention, and FIG. 4B is a schematic representation of the magnetic material collection conveyance method 308 of FIG. 4A. In this example application of the present invention, the first permanent magnet subassembly 152 and the second permanent magnet subassembly 154 are shown. Also shown are the first permanent magnet subassembly north magnet pole 100, first permanent magnet subassembly south magnet pole 102, the first permanent magnet subassembly rotation axis 108, the second permanent magnet subassembly north magnet pole 104, the second permanent magnet subassembly south magnet pole 106, and the second permanent magnet subassembly rotation axis 110.

Using the methods depicted in FIG. 3A, FIG. 3B, and FIG. 3E, magnetic materials can be conveyed towards the target region 404 by orienting the first permanent magnet subassembly 152 and the second permanent magnet subassembly 154 so that the time-averaged second spatial derivative of the magnet field is less than zero which results in the inward directed time-averaged forces 308 acting on the magnetic materials or cores 207. In this example, the coated magnetic cores 207 are administered within the main blood flow 400 and are collected from the blood vessel branches 402, where the rotations of the yoke 132 about the yoke axis 134 results in the coated magnetic cores 207 oscillating, rolling, or tumbling towards the target region. The turbulence of the collecting magnetic material results in new fluidic currents which increase the diffusion rates of co-administered therapeutic agents 406 in the direction the magnetic materials 207 are conveyed. In this example, magnetic materials 207 may be administered either locally or systemically. Example applications include therapeutic conveyance to treat cancer, benign growths, and to deliver neuroprotectants or thrombolytics. In addition, it may be beneficial to attach the therapeutic agent to the magnetic material 207.

Figure 5A:
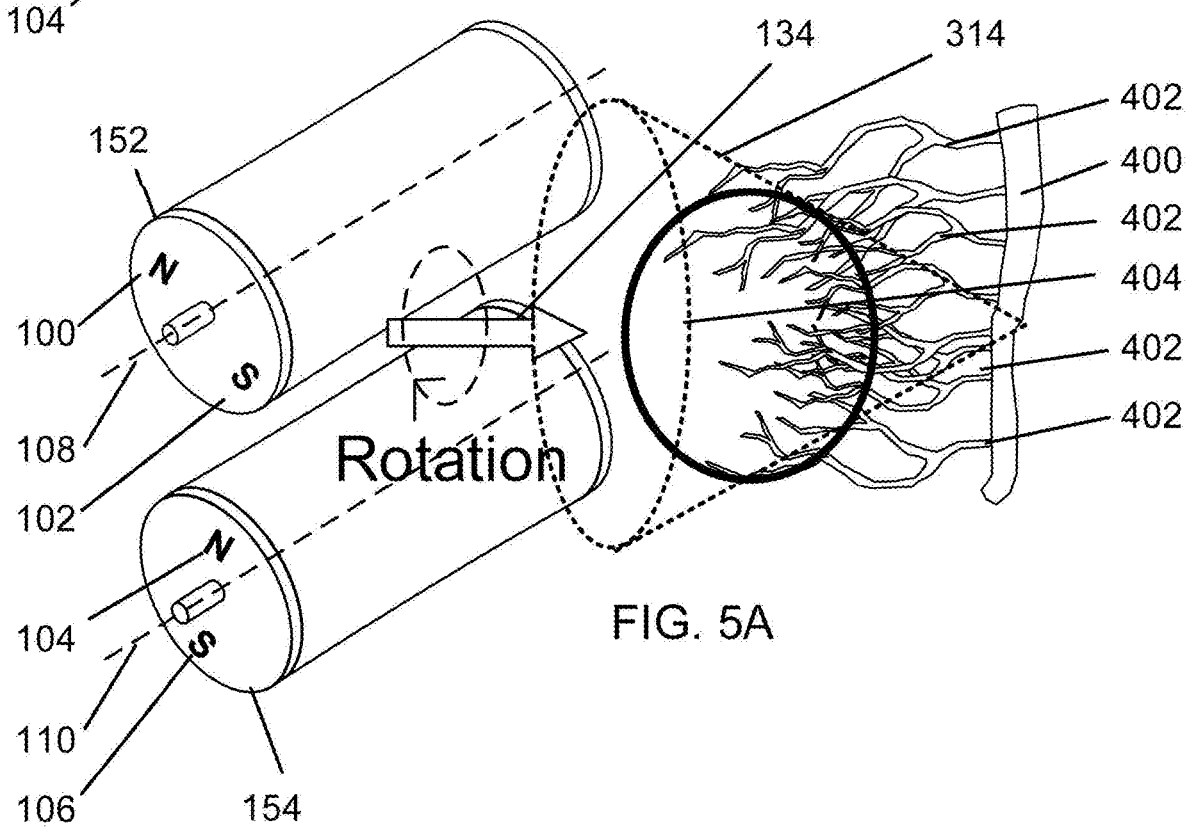
FIG. 5A is a schematic perspective view of a magnetic material dispersal conveyance method within a desired vascularized region using perturbations of the external magnetic field formed by the system of 1A-B in accordance with one aspect of the present invention.
Figure 5B:
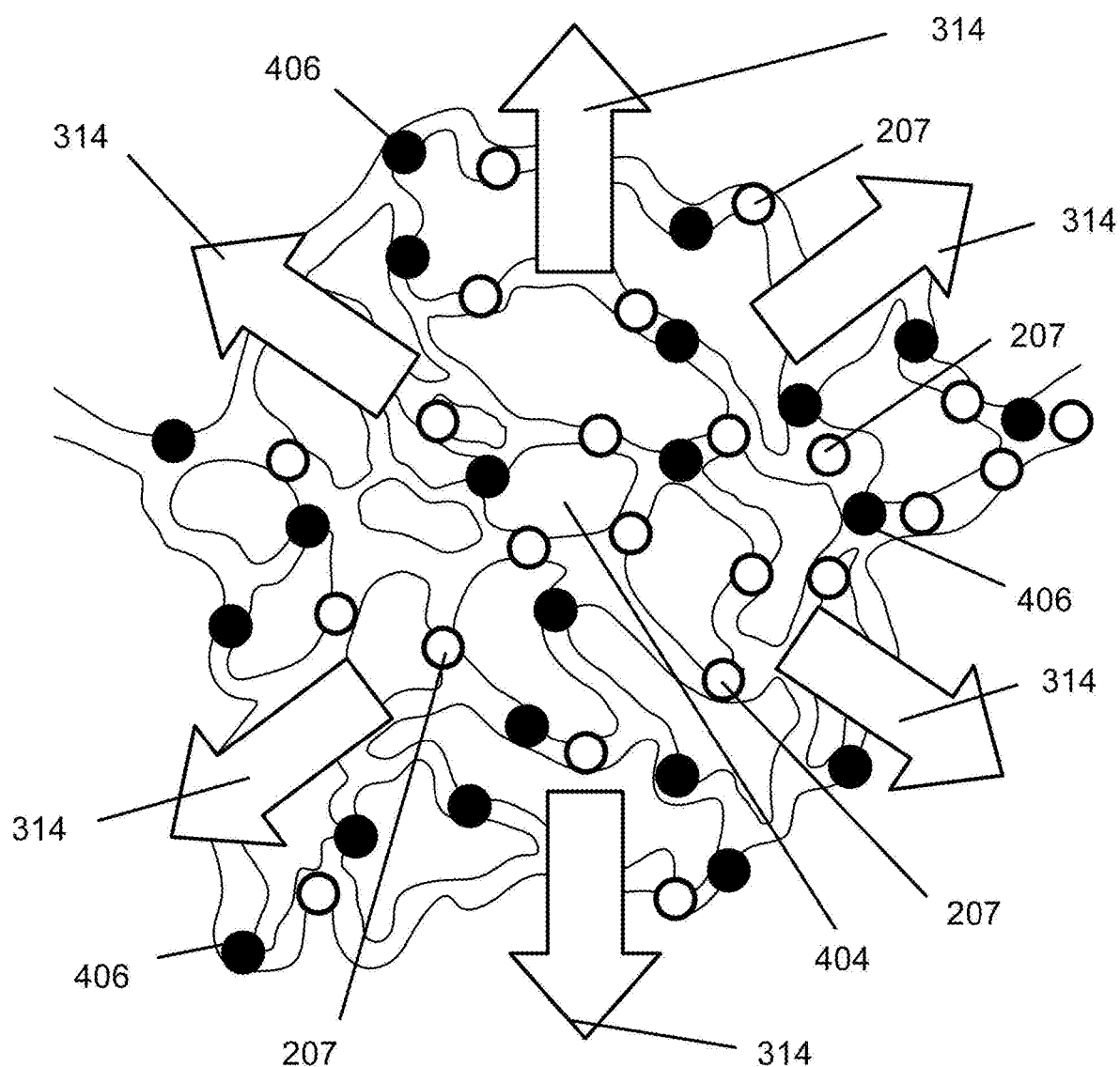
FIG. 5B is a schematic representation of the magnetic material dispersal conveyance method of FIG. 5A.
Figure 6:
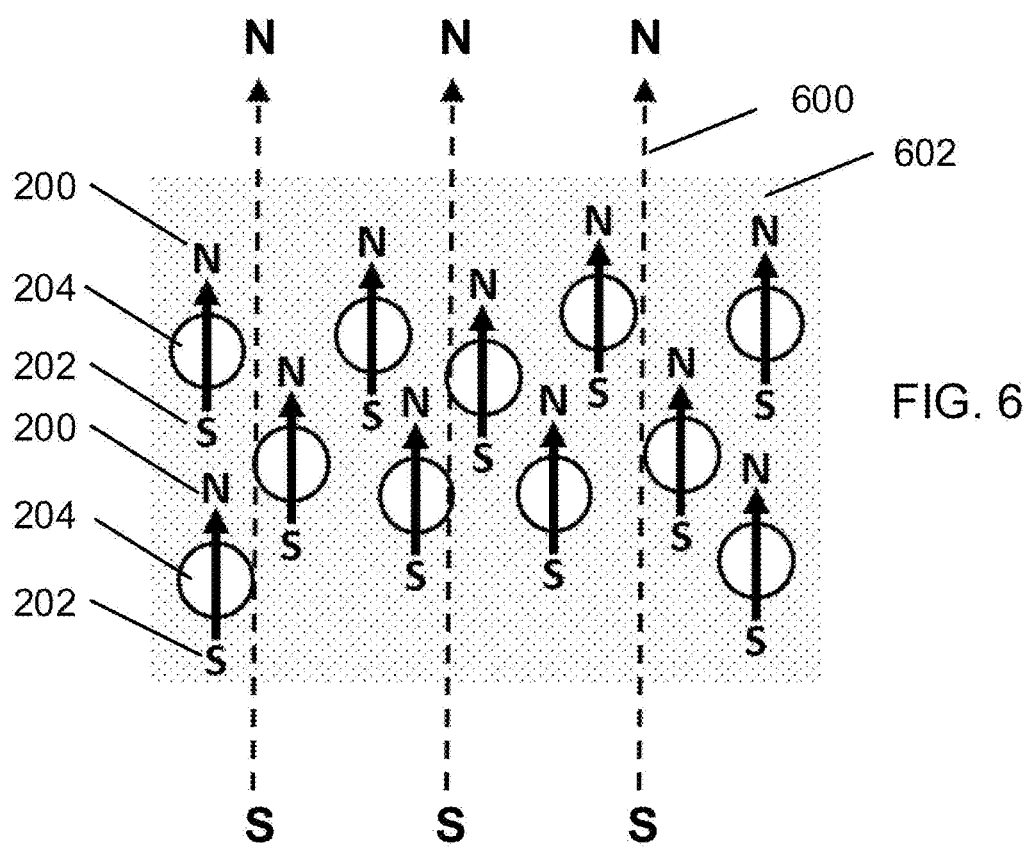
FIG. 6 is a schematic representation of a process to maximize the magnetization of a material in which single crystalline domains are aligned with an external magnetic field formed by the system of 1A-B, which are locked into orientation using a solidifying medium in accordance with one aspect of the present invention.

FIG. 5A is a schematic perspective view of a magnetic material dispersal conveyance method 314 within a desired vascularized region using perturbations of the external magnetic field formed by the system 150 of 1A-B in accordance with one aspect of the present invention, and FIG. 5B is a schematic representation of the magnetic material dispersal conveyance method 314 of FIG. 5A. In this example application of the present invention, the first permanent magnet subassembly 152 and the second permanent magnet subassembly 154 are shown. Also shown are the first permanent magnet subassembly north magnet pole 100, first permanent magnet subassembly south magnet pole 102, the first permanent magnet subassembly rotation axis 108, the second permanent magnet subassembly north magnet pole 104, the second permanent magnet subassembly south magnet pole 106, and the second permanent magnet subassembly rotation axis 110.

In this example, the coated magnetic cores 207 are administered within the main blood flow 400 and are collected from the blood vessel branches 402, where the rotations of the yoke about the yoke axis 134 results in the coated magnetic cores 207 oscillating, rolling, or tumbling towards the target region per the example depicted in FIGS. 4A and B. Then, using the methods depicted in FIG. 3C, FIG. 3D, and FIG. 3F, magnetic materials 207 can be dispersed away from the target region 404 by orienting the first permanent magnet subassembly 152 and the second permanent magnet subassembly 154 so that the time-averaged second spatial derivative of the magnet field is greater than zero which results in the outward directed time-averaged forces 314 acting on the magnetic materials 207. The turbulence of the dispersing magnetic material 207 results in new fluidic currents which increase the diffusion rates of co-administered therapeutic agents 406 or related agents in the direction the magnetic materials 207 are conveyed. In this example, magnetic materials 207 may be administered either locally or systemically. Example applications include therapeutic conveyance to treat cancer, benign growths, and to deliver neuroprotectants or thrombolytics. In addition, it may be beneficial to attach the therapeutic agent to the magnetic material.

FIG. 6 is a schematic representation of a process to maximize the magnetization of a material 204 in which single crystalline domains are aligned with an external magnetic field formed by the system 150 of 1A-B, which are locked into orientation using a solidifying medium 602 in accordance with one aspect of the present invention. Single crystalline magnetic materials are limited in size to, approximately, 100 nm. Formulating larger structures using similar processes results in multiple domains being attributed to the same structure, which tend to demagnetize the larger structure to cancellation interactions between individual magnetic crystals. To create larger structures, a medium 602 can be used to lock the magnetic core material 204 in place while being subjected to a large external magnetic field 600. This external magnetic field 600 maintains the magnetic orientations of the individual magnetic core material 204 while the medium 602 solidifies, where the magnet core material's 204 magnetic north pole 200 and magnetic south pole 202 and aligned with the external magnetic field 600. The final combined material can be shaped as needed for the intended use. For example, ball milling could be used to form structures measuring several hundreds of microns in diameter. Objects of this size are useful in embolizing tumors for TAE and TACE. Example medium 602 material includes a range of polymers.

FIG. 7 is a drawing of permanent magnet angulations which achieve a time-averaged gradient 308 that collects magnetic materials to a desired point in space. More specifically, FIG. 7 is a schematic representation of one example of permanent magnet angulations of the magnets of the system 150 of 1A-B which achieve a time-averaged gradient that collects magnetic materials to a desired point in space for a magnetic material collection conveyance method 308 in accordance with one aspect of the present invention. In this application of the present invention, the first permanent magnet subassembly 152 and the second permanent magnet subassembly 154 are shown. Also shown are the first permanent magnet subassembly North magnet pole 100, first permanent magnet subassembly South magnet pole 102, the first permanent magnet subassembly rotation axis 108, the second permanent magnet subassembly north magnet pole 104, the second permanent magnet subassembly south magnet pole 106, and the second permanent magnet subassembly rotation axis 110. The yoke axis 134 is also depicted about which the yoke 132 rotates, which is aligned with the target region 404.

Calculation of the minimum of the time-averaged second spatial derivative of the magnetic field (which is also negative in value) allows for magnetic materials 207 to be conveyed towards the target region 404. In this example, the first permanent magnet subassembly 152 and the second permanent magnet subassembly 154 each possess approximately 7 kg of magnetic material yielding a magnetic moment of about 500 A-$m^2$. The distance of the first permanent magnet subassembly rotation axis 108 to the second permanent magnet subassembly rotation axis 110 measures 14 cm. The distance from the front surface of the first permanent magnet subassembly 152 and the second permanent magnet subassembly 154 to the target region 404 measures 10.5 cm. The first permanent magnet subassembly 152 is angulated 15 degrees counterclockwise about the first permanent magnet subassembly rotation axis 108 with respect to the vertical axis. The second permanent magnet subassembly 154 is angulated 195 degrees clockwise about the second permanent magnet subassembly rotation axis 110 from vertical. The resulting time-averaged gradient resulting in magnetic material collection 308 extends approximately 7 cm across the target. By moving the two-magnet embodiment 150, or by changing the angulation of the first permanent magnet subassembly 152 and the second permanent magnet subassembly 154, this region can be changed in size to better treat the target region 404.

FIG. 8 is a drawing of permanent magnet angulations which achieve a time-averaged gradient 314 that disperses magnetic materials from a desired point in space. More specifically, FIG. 8 is a schematic representation of one example of permanent magnet angulations of the magnets of the system 150 of 1A-B which achieve a time-averaged gradient that disperses magnetic materials to a desired point in space for a magnetic material dispersal conveyance method 314 in accordance with one aspect of the present invention. In this example application of the present invention, the first permanent magnet subassembly 152 and the second permanent magnet subassembly 154 are shown. Also shown are the first permanent magnet subassembly north magnet pole 100, first permanent magnet subassembly south magnet pole 102, the first permanent magnet subassembly rotation axis 108, the second permanent magnet subassembly north magnet pole 104, the second permanent magnet subassembly south magnet pole 106, and the second permanent magnet subassembly rotation axis 110. The yoke axis 134 is also depicted about which the yoke 132 rotates, which is aligned with the target region 404.

Analogous and effectively the inverse of the above, by calculating the maximum of the time-averaged second spatial derivative of the magnetic field (which is also positive in value), magnetic materials can be dispersed from the target region 404. In this example, the first permanent magnet subassembly 152 and the second permanent magnet subassembly 154 each possess approximately 7 kg of magnetic material yielding a magnetic moment of about 500 A-$m^2$. The distance of the first permanent magnet subassembly rotation axis 108 to the second permanent magnet subassembly rotation axis 110 measures 14 cm. The distance from the front surface of the first permanent magnet subassembly 152 and the second permanent magnet subassembly 154 to the target region 404 measures 10.5 cm. The first permanent magnet subassembly 152 is angulated 52 degrees counterclockwise about the first permanent magnet subassembly rotation axis 108 with respect to the vertical axis. The second permanent magnet subassembly 154 is angulated 52 degrees clockwise about the second permanent magnet subassembly rotation axis 110 from vertical. The resulting time-averaged gradient resulting in magnetic material dispersal 314 extends approximately 3 cm across the target. An unexpected discovery using this example is that a band possessing a diameter of approximately 3 cm is created for which magnetic materials are drawn towards from all directions. By moving the two-magnet embodiment 150, or by changing the angulation of the first permanent magnet subassembly 152 and the second permanent magnet subassembly 154, this region can be changed in size to better treat the target region 404.

The above describes new methods (collectively 308 and 314) for conveying magnetic materials 207 and possibly co-administered therapeutic agents 406 or related agents within the body using an external magnetic field-generating workstation 150. The external magnetic field-generating workstation 150 orients or angulates two (or more) internally-housed magnets so that the magnetic materials 207 (with or without co-administered therapeutic agents 406) can be either simultaneously conveyed towards a user-selected region 404 from one or more directions in method 308 or simultaneously conveyed away from a user-selected region 404 in one or more directions in method 314. This capability is possible by using the optimal or best magnet orientations which maximize the time-averaged second spatial derivative of the combined magnetic field (which is also positive in value) for simultaneously conveying magnetic materials 207 away from a user-selected targeted region 404 in one or more directions, or by using the optimal or best magnet orientations which minimize the time-averaged second spatial derivative of the combined magnetic field (which is also negative in value) for simultaneously conveying magnetic materials 207 towards a user-selected targeted region 404 in one or more directions.

Conveyance of therapeutic agents and/or pharmaceuticals contrasting agents or other related agents is accomplished by two methods. Using one method, therapeutic agents and/or pharmaceuticals are physically associated with or attached to the magnetic materials, such as coating the materials. Using another method, the external magnetic field-generating workstation 150 results in collective motion of the magnetic materials 207 which create new fluidic currents as the magnetic materials 207 roll, rotate, oscillate, vibrate, or tumble within the user-selected targeted region. These motions convey the adjunctively-administered therapeutic agents and/or pharmaceuticals, 406 which increases their conveyance rates over what is otherwise possible. For both methods, the present invention results in the ability to better convey therapeutic agents and/or pharmaceutical faster than otherwise possible and can achieve higher concentrations at the user-selected targeted region 404. This results in improved patient therapy and better outcomes. In addition, the present invention describes the design of unique magnetic material structures which reduce the size of the external magnetic field-generating workstation 150. Further the present invention describes novel magnetic particles which make use of large single-domain crystalline cores, or a core comprised of multiple small single-domain crystalline particles which are mostly magnetically aligned so that the net magnetization is increased, and an optional nonmagnetic coating or surface to reduce the formation of unintended magnetic particle agglomerations. By increasing the effective magnetization of the magnetic material, the required strength of the external magnetic field generated by the magnetic field-generating workstation 150 can be substantially reduced.

The present invention makes use of two (or more) magnets housed within a magnetic field-generating workstation 150 to selectively create regions of magnetic stability or instability. By changing the magnetic field in time, it is possible to either simultaneously convey magnetic materials towards (308) the user-selected targeted region 404 from one or more directions or simultaneously convey magnetic materials away (314) from the user-selected targeted region 404 in one or more directions. For each case, it is not required that the operator or user predefine the direction of magnetic material conveyance. Magnetic material conveyance is accomplished by ensuring the time-averaged second spatial derivative of the magnetic field is positive (for conveying magnetic materials away (314) from the targeted region 404) or negative (for conveying magnetic materials towards (308) the targeted region 404). The time variance enables the magnetic materials to roll, oscillate, vibrate, or tumble along the surface closest to the magnet via traction created against contacting surfaces. The temporal perturbations of the magnetic field overcome static friction forces and allow magnetic materials to be pulled or pushed by the magnetically-generated magnetic force. This allows the operator or user to either convey magnetic materials towards the user-selected targeted region 404 from one or more directions or disperse magnetic materials within the user-selected targeted region 404 in one or more directions.

The best orientations for one or more magnets housed within a magnetic field-generating workstation 150 can be determined so that a preferred time-averaged magnetic stability is generated at the user-selected target region 404. The magnetically-generated time-averaged force, $\langle F \rangle$, generated on a magnetic material, m, by the external magnetic field, B, is given by $\langle F \rangle = \langle \nabla(m \cdot B) \rangle = m \langle \nabla B \rangle$, where it is assumed that the magnetic material aligns with the external magnetic field, and where the outer brackets denote the time average. The referenced coordinate system is described as follows: the y-axis points from the external magnetic field-generating workstation's rotational axis 134 to the user-selected target region 404, and the x-z plane is normal to the y-axis and is centered at or near the middle of the user-selected target region 404.

To generate magnetically-induced traction forces against contacting surfaces, it is required that the magnetic field possess no component in the y-direction so that $B_y = 0$ at or near the user-selected target region 404. Since the magnetic field is rotated about the y-axis, the contributions of the magnetic field in the x- or z-directions are accounted for in calculating the resulting time averages. For simplicity, the x-axis is selected to align with the magnetic field so that $B_y = B_z = 0$ at the user-selected target region in this coordinate system. Off the y-axis, the magnetic field generated by the external magnetic field-generating workstation results in $B_y \neq 0$. As the magnets housed within the magnetic field-generating workstation are together rotated about the y-axis, magnetic field perturbations are generated over or near the user-selected targeted region 404 which cause the magnetic materials to roll, rotate, oscillate, vibrate, or tumble. The time-averaged magnetic stability at the user-selected target region 404, $\langle S \rangle$, is given by $\langle S \rangle = \langle \nabla \cdot F \rangle$. It follows that $\langle S \rangle = \langle m \nabla^2 B_x \rangle$. Using the fact that $\langle \nabla^2 B^2 \rangle = 2 \langle (\nabla B_x)^2 \rangle + \langle B_x \nabla^2 B_x \rangle$, and that $\langle (\nabla B_x)^2 \rangle = 0$ at the user-selected target region 404, it follows that $$\langle m \nabla^2 B_x \rangle = \left\langle \frac{m}{2B_x} \nabla^2 B_x^2 \right\rangle.$$

If the magnetic material is magnetically permeable so that m–αB, where α is the magnetic permeability constant, then $$\langle m \nabla^2 B_x \rangle = \frac{\alpha}{2} \langle \nabla^2 B_x^2 \rangle.$$

For an external magnetic field-generating workstation comprised of N magnets, it follows that $$\langle m\nabla^2 B_x\rangle = \frac{\alpha}{2}\sum_{i=1}^{N}\langle \nabla^2 B_{i,x}^2\rangle.$$

From this approach it has been discovered that the optimal or best angle for each magnet, $\theta_i$, is independent of all other magnet angles. Thus, the optimal or best magnet angle can be found by solving for $$\frac{\partial}{\partial \theta_i}\langle \nabla^2 B_{i,x}^2\rangle = 0$$

for each of the N magnets. To convey magnetic materials toward the user-selected target region requires $\langle \nabla^2 B_{i,x}^2\rangle$ be less than zero with respect to $\theta_i$ for each of the N magnets. Likewise, to convey magnetic materials away from the user-selected target region requires $\langle \nabla^2 B_{i,x}^2\rangle$ be greater than zero with respect to $\theta_i$ for each of the N magnets.

In one example use of the present invention, neuroprotectants are conveyed to an ischemic region in the event of AIS using two magnets housed within the external magnetic field-generating workstation 150. The present invention allows physicians (i.e., the user or operator) to better convey neuroprotective therapeutic agents towards a targeted region 404 from one or more directions without knowledge of the orientation of the occluded vessel by determining the best orientations of two permanent magnets which are angulated to minimize the second spatial gradient of the magnetic field (which is also negative in value) at the desired region. By rotating the magnet assembly around the magnet subassembly's yoke axis 134 (i.e., the y-axis) in time, magnetic materials (e.g., magnetic nanoparticles) can be made to roll, rotate, oscillate, vibrate, or tumble. As a result, the magnetic materials use the magnetically-generated traction force to roll, rotate, oscillate, vibrate, or tumble against contacting surfaces while being subjected to an externally-generated time-averaged radial force which conveys the magnetic materials towards the user-selected target region from one of more directions. A useful analogy is to consider a large cement ball, which requires far less force to roll than to drag. This approach is considerably more efficient than historical approaches which used a magnet's weak pulling force (which is generated via the magnetic gradient). It is important to note that unlike the Pulse Therapeutics technologies in which a single magnet is used to convey magnetic particle agglomerates in an end-over-end motion in a direction specified by the operator (which must also align with the occluded vessel), the present invention does not require a plane of rotation to be pre-identified which must align with the user-selected targeted vessel.

For this example application, in which neuroprotectants are better conveyed to the region of ischemia, a useful magnetic material would include the use of iron oxide nanoparticle (IONP) structures, which may possess a coating, and which are intravascularly administered and then captured near the user-selected targeted region. By designing the IONP structures to be single-crystalline (as much as is reasonably possible) and ferromagnetic, the external magnetic field requirements can be greatly reduced and the IONP structures can be more easily conveyed within slow-moving or stagnant blood flow. Alternatively, the IONP structure may be composed of many single-crystalline domains which are majority aligned so as to increase the net magnetization. If a coating or surface is applied to the IONP structure, it may be advantageous to make the coating or surface thick enough to minimize interaction forces between IONP structures so that agglomerates do not form or that potential agglomerates are dispersed by the shearing forces of blood flow. However, the coating or surface should be thin enough to preserve a strong magnetization for the overall IONP structure so that the external magnetic field-generating workstation 150 is as small as possible. As blood flow carries the IONP structures near the ischemic territory, use of the external magnetic field-generating workstation enables some of the IONP structures to be magnetically rolled, rotated, oscillated, vibrated, or tumbled into the stagnant blood columns at the interface between flowing and stagnant blood flow. The mechanical manipulation of the magnetic material creates new fluidic currents towards the user-selected target region 404 from one of more directions, which can adjunctively convey intravascularly-administered neuroprotective agents towards the user-selected target region from one of more directions. This is achieved without the need to specify a preferred direction of magnetic material conveyance in advance.

In use, this example embodiment of the present invention could be deployed at first medical contact following the successful strategies implemented in neuroprotectant stroke studies. Within the ambulance, the external magnetic field-generating workstation 150 would be placed next to the affected brain hemisphere and activated for approximately an hour. The IONPs and neuroprotectant could, therefore, be administered and therapy applied during transport. The external magnetic field-generating workstation 150 could be deactivated during intra-hospital transport. In addition, this example embodiment of the present invention may provide similar benefits for head trauma and in conveying thrombolytic agents to clot in the treatment of stroke.

A benefit of this approach using the present invention is that attachment of the neuroprotectant to the IONP structure is not a requirement for efficacy. Multiple neuroprotectants could be adjunctively used together and without modification, thereby increasing the number of interdicted ischemic injury pathways. In other example uses of the present invention, the neuroprotectant could be attached to the IONP structure. A benefit of such an approach is the reduction of dose-related systemic neuroprotectant toxicity effects given that dose-dependent efficacy could be maintained or increased using a lower neuroprotectant dose.

For this example embodiment, the optimal or best angles for a two-magnet assembly follow from minimizing $\langle \nabla^2 B_{i,x}^2\rangle$ with respect to $\theta_i$ for each of the N magnets (where i is the index of one of the N magnets), with the requirement that $\langle \nabla^2 B_{i,x}^2\rangle < 0$. As a result, a "magnetic trap" (i.e., a negative value for the time-averaged second spatial derivative of the magnetic field) is formed that rolls, rotates, oscillates, vibrates, or tumbles the IONP structures towards the user-selected targeted region from one or more directions. For this example embodiment, it is possible that an ultrasound-sized, portable assembly weighing less than 50 kg (50 mT at target, cycled at 3-10 Hz) will be able to efficiently collect the IONP structures up to 15 cm from the system's surface, while generating a magnetic field 30× weaker field than those associated with a 1.5 T MR unit.

In general, hospital guidelines limit non-study personnel to magnetic fields less than 0.5 mT. An advantage of this example embodiment of the present invention is the ability to reorient the magnets housed within the external magnetic field-generating workstation 150 to substantially cancel the combined magnetic field. This enables safer and easier intra-hospital transport and reduces the combined magnetic field in populated areas or when the system 150 is being shipped or stored.

In another example use of the present invention, liver tumors can be treated, where the present invention allows physicians to better convey embolization and chemoembolization beads for the purposes of better embolizing a tumor and/or delivering chemotherapeutic agents within the user-selected targeted region 404 in one or more directions without required prior knowledge of the orientations of the intra-tumor and neighboring blood vessels. The present invention allows specification of the orientations of two permanent magnets housed within the external magnetic field-generating workstation 150 which are oriented to generate a positive value for the second spatial gradient of the magnetic field at the desired region. By rotating the magnet assembly around the magnet subassembly's yoke axis 134 in time, magnetic materials (e.g., magnetic nanoparticles, IONP structures, magnetic embolization beads) can be made to roll, rotate, oscillate, vibrate, or tumble. As a result, the magnetic materials use the magnetically-generated traction force to roll, rotate, oscillate, vibrate, or tumble against contacting surfaces while being subjected to an externally-generated time-averaged radial force which disperses the magnetic materials throughout the user-selected target region 404 in one of more directions. This allows embolization material to be better conveyed throughout a tumor in a way not previously possible This approach is considerably more efficient than historical approaches which used a magnet's weak pulling force (i.e., via the magnetic gradient). And unlike the inventions of Pulse Therapeutics in which a single magnet is used to convey magnetic particle agglomerates in an end-over-end motion in a direction specified by the operator (which aligns with the occluded vessel), the present invention does not require a plan of rotation to be identified which aligned with the user-selected targeted region.

For this example embodiment of the present invention, the optimal or best orientations or angles for a two-magnet assembly housed within the external magnetic field-generating workstation 150 follow from maximizing $\langle \nabla^2 B_{i,x}^2 \rangle$ with respect to $\theta_i$ for each of the N magnets (where i is the index to the referenced magnet), with the requirement that $\langle \nabla^2 B_{i,x}^2 \rangle > 0$. As a result, a "dispersal region" is formed that rolls, rotates, oscillates, vibrates, or tumbles the magnetic materials throughout the user-selected targeted region in one or more directions. For this example embodiment, it is envisioned that an ultrasound-sized, portable assembly 150 weighing less than 50 kg (50 mT at target, cycled at 3-10 Hz) will efficiently disperse magnetic materials up to 15 cm from the system's surface, generating a magnetic field 30× weaker field than those associated with a 1.5 T MR unit.

It is envisioned that this example embodiment of the present invention will follow the same workflow as TAE/TACE. The external magnetic field-generating system is predicted to be the same size as a portable ultrasound unit and will be located within 15 cm of the user-selected targeted tumor. The external magnetic field-generating system will be activated during administration of the magnetic materials (e.g., magnetic nanoparticles, magnetic embolization beads, IONP structures), with differently-sized magnetic embolization beads used over the course of magnetic embolization therapy if desired. The use of different magnetic embolization bead sizes ensures that a range of intra-tumor vessel sizes can be accessed, embolized, and/or treated. It may be useful to design the magnetic embolization beads to be radiopaque so that their placement during the procedure using x-ray image guidance is possible. Post magnetic embolization bead administration, the external magnetic field-generating system will continue to operate to better disperse magnetic materials within the tumor's volume. It is also possible that non-magnetic embolization beads could be used alongside the magnetic embolization beads, where the magnetic conveyance of the magnetic embolization beads using the external magnetic field-generating workstation results in new fluidic currents within or near the use-selected targeted region which better conveys the nonmagnetic embolization beads within or near the use-selected targeted region.

Another invention associated with the present invention pertains to the novel design and formulation of the coated IONPs. While IONPs are generally biocompatible, hypersensitivity reactions can occur. An IONP coating can reduce such interactions. Historically, many approaches rely on applying the coating during IONP formulation. These methods are effective in creating large (>100 nm) multi-crystalline cores. However, the IONP magnetic cores tend to be agglomerates of many small (e.g., ~10 nm) IONP crystals. This results in a loss of overall IONP structure magnetization due to demagnetization interactions between the individual IONP crystals. In addition, these IONP materials tend to be superparamagnetic, which further reduces the net magnetization. To magnetically manipulate such small magnet core materials, strong external magnetic fields are required, which can be on the order of those produced by an MR system. In contrast to these historical approaches, the present invention described the use of novel coated IONPs, where each coated IONP is comprised of a single-domain crystalline magnetite ($Fe_3O_4$) core to which a nonmagnetic material or coating is applied. An example of magnetic material which can be used as the core of the IONP structure is magnetite (chemical form of $Fe_3O_4$), which possesses a long biocompatibility history. An example coating or surfacing material that has been shown to be historically biocompatible is polyethylene glycol (PEG). A PEG coating or surface can reduce acute hypersensitivity reactions, prevent IONP structure agglomerations, and extend the IONP structure's blood-plasma half-life. PEG is a preferred coating material which is widely used in commercially-available parenteral formulations as an inert carrier. In general, PEG molecules cannot be metabolized by the body and are excreted intact via the urine and feces. Additionally, they are known to be nonmagnetic, cytotoxicity negative, non-immunogenic, and non-antigenic. However, when used as a coating or surface on the magnetic core, the PEG coating must be thin enough to minimally impact the IONP structure's net magnetization so that manipulation using weaker magnetic fields generated by the external magnetic field-generating workstation is possible.

Another invention related to the present invention pertains to the formulation of the magnetic embolization beads. Extending the principles behind sintering rare-earth magnets, a plurality of small magnetite particles within the embolization bead can be aligned under a magnetic field during formulation. Without this process, a large proportion of the single-phase iron crystals will magnetically cancel each other, thereby requiring a stronger external magnetic field and a larger external magnetic field-generating system to exert control.

In general, the numerical details of this process can vary, depending on the nature of the therapeutic need, the disease condition, the design and formulation of the magnetic materials, and the design and use of the external field-generating workstation 150. Preliminary investigations support that a wide range of rotation frequencies are likely to be effective using a range of magnetic field strengths generated by external field-generating workstation 150. The permanent magnets enclosed in the external field-generating workstation 150 are expected to fit within in a volume of approximately one cubic foot. The use of electromagnetic coils in place of the permanent magnets is likely to require a larger volume but can achieve similar effects.

Two example applications relating to the present invention include the delivery of neuroprotectants for the treatment of acute ischemic stroke (AIS) and the delivery of trans-arterial embolization (TAE) and trans-arterial chemoembolization (TACE) beads for the treatment of tumors and other adverse vascularized regions.

AIS is the result of a blood clot in a cerebral artery. Each year, AIS impacts nearly 700,000 Americans. It is the leading cause of long-term disability and the $5^{th}$ leading cause of death in the US. Deprived of blood, brain tissue rapidly dies. Thus, time to reperfusion is critical in preventing death and improving neurological outcomes. While annual costs related to ischemic stroke are already high in the US, they are projected to further increase to $183B by 2030. AIS victims have few options. Intravascular (IV) administration of tissue plasminogen activator (tPA) remains the standard of care for AIS, with thrombectomy recommended for proximal large vessel occlusions in the anterior circulation (indicated up to 8 hours post stroke onset). However, 60% of all AIS victims are ineligible for any intervention primarily due to procedure-related intracranial hemorrhage risks. The excluded treatment populations consist of mild (30%) and wake-up strokes (30%), which are normally treated with palliative care. Of the remaining 40%, less than 10% receive intervention in practice due to contraindications and system-wide delays. Thus, more than 90% of AIS victims receive no intervention. Time delays continue to represent a major limitation. Ambulance transportation ranges from 40 min to 120 min. Stroke onset to thrombolysis averages nearly 2 hours. And, stroke onset to thrombectomy averages nearly 4 hours. Of those receiving intervention, only one-third show a relative improvement in their outcomes. Thus, there is an urgent need for therapies which preserve the viability of brain tissue for as long as possible for all AIS victims.

Neuroprotectants represent a potentially powerful tool in prolonging brain viability. Neuroprotectant research has been active for over 40 years, resulting in more than 1,500 experimental and clinical publications between 2002 and 2008. Unlike neurons located in the infarcted core, neurons located within the ischemic penumbra are more likely to recover at early time points. Neuroprotective agents work by limiting injury to neurons by interrupting the cellular, biochemical, and metabolic processes that mediate cerebral-tissue injury during or after ischemia. Many neuroprotectants attempt to modulate neuronal receptors to reduce release of excitatory neurotransmitters, which otherwise aggravate early neuronal injury. One advantage of neuroprotectants is their ability to be administered at first medical contact given that many have been shown to be safe and potentially beneficial in hemorrhagic stroke victims as well as in those suffering from AIS. In contrast, thrombolysis must be delayed until stroke is confirmed using baseline imaging (via CT or MR).

Despite that rigorous animal models of brain ischemia provide clear evidence that a high-degree of brain protection is possible, more than 70 neuroprotective clinical studies have failed to reproduce these results in phase 3 trials. Example agents include GV150526, magnesium, Citicoline, NXY-059, and albumin. It is widely believed that the use of reduced neuroprotectant doses and delayed neuroprotectant administration hindered many of these studies. While animal studies support a 4-hour neuroprotection window, human AIS victims tend to be older with several comorbidities that may limit benefit. To better address the impact of ischemic time, a Phase III study was launched to evaluate the use of magnesium sulfate at first medical contact (FAST-MAG). Despite showing no neurological benefit at 90-days, FAST-MAG investigators felt that the slow uptake of magnesium sulfate across the blood-brain barrier may have affected efficacy. Additionally, the smaller ischemic volumes and shorter vessel lengths in animals may not fully model neuroprotectant diffusion and final neuroprotectant concentrations in humans.

The AIS-induced change in hemodynamics limits neuroprotectant access to ischemic regions. When a clot occludes flow within a cerebral vessel, drug conveyance is limited to a biological diffusion rate similar to that of proteins in blood (~2 mm/hr) due to the formation of stagnant blood columns near the clot. The smaller brains of animals used in stroke ischemic models are associated with shorter vessels lengths. Thus, neuroprotectants can access a greater ischemic volume and achieve higher concentrations in animals compared to larger human anatomy. This fluid-mechanical limitation may help explain why neuroprotectants have underperformed in AIS clinical studies. This consequence of AIS represents a renewed opportunity for neuroprotectants to demonstrate their potential benefit. A platform such as system 150 which reliably delivers neuroprotectants to ischemic regions represents a breakthrough in neuroprotection, especially as it is not strictly limited to one of the more-than 70 neuroprotectants already investigated to date (several of which have already demonstrated safety in Phase III AIS studies). Furthermore, the system 150 allow the simultaneous use of multiple neuroprotective agents which increase the number of interdicted ischemic injury pathways.

Another example application of the present invention pertains to the treatment of liver cancer. Cancer remains the $2^{nd}$ leading cause of death in the United States (US) and accounts for 1 of every 4 deaths. More than 600,000 Americans are expected to die of cancer in 2018, where the incidence is 159 new diagnoses per 100,000 people. Annual US expenditures for cancer care totaled nearly $125 billion in 2010 and are predicted to reach $156 billion by 2020. Worldwide, cancer accounts for nearly 10 million annual deaths. While chemotherapy is effective, there remain several cancer subtypes associated with a low 5-year survival. These include pancreatic (8%), liver (18%), lung (18%), esophageal (19%), stomach (31%), and brain (34%). Together, these represent 400,000 new cancer incidences each year and 270,000 deaths. The low survival rates reflect that only a small population is eligible for tumor resection and organ transplant.

Hepatocellular carcinoma is the most common form of primary liver cancer, with over 500,000 new diagnoses each year. It is the $6^{th}$ most common cancer worldwide and the $3^{rd}$ most common cause of cancer-related deaths. While cancer deaths have decreased, liver cancer death rates have increased over the last 30 years (annual increase 2.6% worldwide and 4.5% in the US). Although some liver cancer patients may be candidates for surgery, most are contraindicated to surgical interventions due to complications associated with advancement of the disease state. These patients have few options for treatment.

Chemotherapy has shown limited benefit for liver and colorectal primary and metastatic tumors, where more than half of those diagnosed with colorectal cancer will develop liver metastases in their lifetime. In general, chemotherapeutic treatment of advanced hepatocellular carcinoma has shown limited effectiveness, with a less than 20% response rate and less than a one-year survival benefit. For example, a randomized controlled trial was conducted of doxorubicin versus best supportive care for subjects diagnosed with advanced hepatocellular carcinoma confirmed only a modest survival benefit (10.6 weeks improvement versus 7.5 weeks for best in care, P<0.05). More recent studies using newer therapeutic agents also show low benefit. The standard therapy for metastatic colorectal cancer (fluorouracil in combination with leucovorin) yields less than a 15% response rate and a median survival time of less than 10 months.

Trans-arterial embolization has emerged as a remaining option for those diagnosed with hepatocellular carcinoma. In recent clinical studies, trans-arterial embolization (TAE) and trans-arterial chemoembolization (TACE) have shown promise in the treatment of liver cancer in terms of efficacy (2-year reduction in mortality) and safety (5% less morbidity and 0.6% less mortality). Both TAE and TACE are well-suited for hepatocellular carcinoma. The liver is atypical in that it possesses two blood supplies. While most normal liver cells are fed by branches of the portal vein, liver tumors are fed by branches off the hepatic artery. Thus, blocking the branch of the hepatic artery supplying the tumor results in killing cancer cells while leaving the healthy cells relatively unharmed. For both TAE and TACE, the vessels supplying blood to the tumor are embolized using a catheter-delivered material, thereby promoting cell death. For TACE, a chemotherapeutic is incorporated with the embolic material. In both procedures, a catheter is guided under x-ray imaging to the artery feeding the tumor. Once positioned, embolization beads are administered over 10-20 minutes. Typically, preferred embolization beads measure in the range of 40-1000 um. TACE is the gold standard of care for patients with intermediate-stage hepatocellular carcinoma who show preserved liver function, where the median survival improvement over best supportive care is 4 months. Interestingly, recent studies support that TAE and TACE are equally effective in the management of patients with hepatocellular carcinoma. In fact, the absence of chemotherapy is believed to make TAE better tolerated in patients with borderline liver function. Together, TAE and TACE represent a $4.8B worldwide opportunity.

Despite its use for over two decades, TAE and TACE remain unstandardized procedures, with a range of options in terms of bead size and formulation, the choice and dose of chemotherapeutic agents, and the time interval between procedures. A fundamental limitation of existing TAE and TACE is that embolization of the tumor's supply vasculature is limited by vessel geometry, tortuosity, and access, where not all vessels can be reliably occluded. As a result, intratumor hemodynamics cannot disperse embolization beads (and chemotherapeutics, when used) throughout the tumor. In these cases, surviving tumor regions are likely to regrow. Potentially better outcomes are expected to be seen with the system 150 where physicians are able to exert control over the delivery of embolization beads and direct them throughout the tumor's vasculature to ensure more thorough occlusion of blood flow and chemotherapeutic delivery.

As shown above a two magnet system 150 with two identical strength magnets having the first permanent magnet rotation axis 108 and the second permanent magnet rotation axis 110 equidistant from the yoke axis 134 and parallel to each other and in a plane which is perpendicular to the yoke axis 134, yields advantages in the operation of the system 150 as discussed above. However variations may be made in this arrangement, for example additional magnetic pairs could be added, with each of the pairs having their own axis of rotation which are also equidistant from the yoke axis 134 and parallel to eachother in a plane that is perpendicular to the yoke axis 134. Unequal strength magnets are also possible that are rotated on axes that are parallel to each other, and in a plane that is perpendicular to the yoke axis, but are not equidistant from the yoke axis 134. Skewing the rotation axis 108 and 110 relative to the yoke axis 134 are possible as well, but this modification eliminates some of the operational advantages of the system 150. It will be understood that some of the methods of conveyance discussed herein are possible with a system 150 having single magnet rotatable on an axis of rotation that is skewed relative to the associated yoke axis 134, but there are operational advantages to a system 150 implementing equal strength magnet pairs that are rotated on respective axes 108 and 110 that are arranged parallel to each other and within a plane that is perpendicular to the yoke axis and which axes are equidistant from the yoke axis 134.

The present invention convers a range of magnetic materials conveyed by the external field-generating workstation 150. These include but are not limited to the following: magnetic embolization beads, magnetic nanoparticles, IONP structures, coated IONP structures, coated and uncoated IONP structures using magnetite as the core material (both single-domain and multi-domain crystalline structures), magnetic devices that can be conveyed within the lumens of the body, carbonyl iron, magnetic embolization gels and foams, and magnetic materials intended to treat aneurysm.

The present invention convers a range of therapeutic agents or pharmaceuticals conveyed by the external field-generating workstation. These include but are not limited to the following: embolization materials, neuroprotectants, thrombolytic agents, anti-cancer agents, stem cells, gene-delivery therapeutics, contrast agents, antibiotics, anticoagulants, and microbubbles. Conveyance of these agents may be achieved via conjugation to the magnetic material or via the creation of new fluidic currents generated by the manipulation magnetic material which adjunctively conveys the therapeutic agent or pharmaceutical using the external magnetic field-generating workstation.

The present invention convers a range of therapeutic applications. These include but are not limited to the following: cancerous growths, benign growths, stroke, distal blood clots, head trauma, glaucoma, macular degeneration, arteriovenous malformations, blood clots in the eye, deafness, frost bite, myocardial infarction, pulmonary embolism, and cancer of the brain, lungs, prostate, kidney, liver, pancreas, intestine, stomach, throat, tongue, bone, and bladder.

The present invention also describes positioning and/or orienting the individual magnets housed within the external field-generating workstation 150 so that the magnetic fields generated by each of the housed magnets are oriented so that the combined magnetic field cancels. This enables easier and safer transport, shipment, and storage in populated areas.

The present invention also considers the use of one or more magnets contained within the external field-generating workstation to achieve the intended delivery of the therapy. The magnets employed may be permanent magnets or electromagnets. The magnets may be separately or collectively articulated using a range of known articulators.

The present invention also considers conjugating therapeutics or pharmaceuticals to the magnetic materials for the purpose of increasing efficacy (by increasing drug concentration at the target) and/or safety (by lowering systemic therapeutic toxicity). Bound agents or agents associated with the magnetic materials could be released using external energies to achieve better therapies. These modalities include, but are not limited to, liposomal release, light-based activation, ultrasound, magnetic agitation, and hyperthermia.

While the invention has been shown in several particular embodiments it should be clear that various modifications may be made to the present invention without departing from the spirit and scope thereof. The scope of the present invention is defined by the appended claims and equivalents thereto.

What is claimed is:

1. A system for conveyance of therapeutic agents using a configurable magnetic field comprising:
    at least two magnet subassemblies, each magnet subassembly with a north magnetic pole and a south magnetic pole, wherein each magnet subassembly is mounted for rotation about a magnet subassembly rotation axis that varies the orientation of the north magnetic pole and the south magnetic pole of the magnet subassembly;
    a yoke supporting each magnet subassembly and mounted for rotation about a yoke rotation axis that is offset from each magnet subassembly rotation axis, wherein rotation of the yoke configures a collective magnetic field of the system, wherein the respective magnet subassembly rotation axes of the at least two magnet subassemblies are offset on different sides of the yoke rotation axis;
    a plurality of magnetic materials associated with therapeutic agents to be conveyed by the system; and
    wherein the plurality of magnetic materials and associated therapeutic agents to be conveyed by the system are influenced by the collective magnetic field to either be conveyed simultaneously towards a user selected region from multiple directions or conveyed simultaneously away from the user selected region in multiple directions by magnet orientations which minimize or maximize the time-averaged second spatial derivative of the combined magnetic field.

2. The system for conveyance of therapeutic agents using a configurable magnetic field according to claim 1, wherein the magnet subassembly rotation axes of the at least two magnet subassemblies are equidistant from the yoke rotation axis.

3. The system for conveyance of therapeutic agents using a configurable magnetic field according to claim 2, wherein the magnet subassembly rotation axes of the at least two magnet subassemblies are parallel to each other and aligned in a common plane which is perpendicular to the yoke rotation axis.

4. The system for conveyance of therapeutic agents using a configurable magnetic field according to claim 3, wherein each magnet subassembly has the same magnetic strength.

5. The system for conveyance of therapeutic agents using a configurable magnetic field according to claim 1, wherein the at least two magnet subassemblies comprises a pair of permanent magnet subassemblies each with an actuator for rotation of the permanent magnet subassembly about the magnet subassembly rotation axis.

6. The system for conveyance of therapeutic agents using a configurable magnetic field according to claim 5, wherein the first permanent magnet rotation axis and the second permanent magnet rotation axis are equidistant from the yoke rotation axis and further including a yoke actuator for rotation of the yoke about the yoke rotation axis.

7. The system for conveyance of therapeutic agents using a configurable magnetic field according to claim 1, wherein at least some of the magnetic materials associated with therapeutic agents comprise crystalline magnetite cores to which a nonmagnetic material coating is applied.

8. A method for conveyance of therapeutic agents using a configurable magnetic field comprising:
    providing a magnetic field generating workstation comprising at least two magnet subassemblies, each magnet subassembly with a north magnetic pole and a south magnetic pole, wherein each magnet subassembly is mounted for rotation about a magnet subassembly rotation axis that varies the orientation of the north magnetic pole and the south magnetic pole of the magnet subassembly, and a yoke supporting each magnet subassembly and mounted for rotation about a yoke rotation axis that is offset from each magnet subassembly rotation axis, wherein rotation of the yoke configures a collective magnetic field of the system;
    aligning the yoke with a user selected region within a subject;
    introducing a plurality of magnetic materials and associated therapeutic agents to be conveyed by the system into the subject;
    orientating each magnet subassembly by rotation about a magnet subassembly rotation axis to a specific angular location;
    configuring the collective magnetic field of the magnetic field generating workstation by rotation of the yoke about the yoke axis; and
    wherein the plurality of magnetic materials and associated therapeutic agents to be conveyed by the system are influenced by the collective magnetic field to either be conveyed simultaneously towards the user selected region from multiple directions or conveyed simultaneously away from the user selected region in multiple directions by magnet orientations which minimize or maximize the time-averaged second spatial derivative of the combined magnetic field.

9. The method for conveyance of therapeutic agents using a configurable magnetic field according to claim 8, wherein the configuring the collective magnetic field of the magnetic field generating workstation by rotation of the yoke about the yoke rotation axis includes wherein the plurality of magnetic materials and associated therapeutic agents to be conveyed by the system are influenced by the collective magnetic field to be conveyed towards the user-selected region from multiple directions.

10. The method for conveyance of therapeutic agents using a configurable magnetic field according to claim 9, wherein the collective magnetic field influencing the plurality of magnetic materials and associated therapeutic agents to be conveyed towards the user selected region from multiple directions is formed by magnet orientations which minimize the time-averaged second spatial derivative of the combined magnetic field.

11. The method for conveyance of therapeutic agents using a configurable magnetic field according to claim 8, wherein the configuring the collective magnetic field of the magnetic field generating workstation by rotation of the yoke about the yoke rotation axis includes wherein the plurality of magnetic materials and associated therapeutic agents to be conveyed by the system are influenced by the collective magnetic field to be conveyed away from the user selected region in multiple directions.

12. The method for conveyance of therapeutic agents using a configurable magnetic field according to claim 11, wherein the collective magnetic field influencing the plurality of magnetic materials and associated therapeutic agents to be conveyed away from the user selected region in multiple directions is formed by magnet orientations which maximize the time-averaged second spatial derivative of the combined magnetic field.

13. The method for conveyance of therapeutic agents using a configurable magnetic field according to claim 8, wherein at least some of the plurality of magnetic materials are physically associated with therapeutic agents.

14. The method for conveyance of therapeutic agents using a configurable magnetic field according to claim 8, wherein at least some of the associated therapeutic agents are adjunctively-administered with the separate magnetic materials and conveyed by fluidic currents formed by the movement of the magnetic materials.

15. The method for conveyance of therapeutic agents using a configurable magnetic field according to claim 8, wherein at least some of the magnetic materials associated with therapeutic agents comprise crystalline magnetite cores to which a nonmagnetic material coating is associated.

16. The method for conveyance of therapeutic agents using a configurable magnetic field according to claim 8, wherein the at least one magnet subassembly of the workstation comprises a pair of permanent magnet subassemblies each with a motor for rotation of the permanent magnet subassembly about the magnet subassembly rotation axis, wherein the magnet subassembly rotation axes of the at least two permanent magnet subassemblies are offset on different sides of the yoke rotation axis.

17. The method for conveyance of therapeutic agents using a configurable magnetic field according to claim 16, wherein the first permanent magnet rotation axis and the second permanent magnet rotation axis of the workstation are equidistant from the yoke rotation axis and parallel to each other and aligned in a plane which is perpendicular to the yoke rotation axis and further including a yoke motor for rotation of the yoke about the yoke rotation axis.

* * * * *